(12) United States Patent
Lundahl et al.

(10) Patent No.: US 12,296,011 B2
(45) Date of Patent: May 13, 2025

(54) METHODS FOR PHOTODYNAMIC THERAPY

(71) Applicant: Sun Pharmaceutical Industries, Inc., Princeton, NJ (US)

(72) Inventors: Scott Lundahl, Lexington, MA (US); Michael Guttadauro, Carlisle, MA (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 0 days.

(21) Appl. No.: 18/313,162

(22) Filed: May 5, 2023

(65) Prior Publication Data

US 2023/0321243 A1 Oct. 12, 2023

Related U.S. Application Data

(60) Continuation of application No. 17/876,224, filed on Jul. 28, 2022, now Pat. No. 11,690,914, which is a
(Continued)

(51) Int. Cl.
*A61K 41/00* (2020.01)
*A61K 9/00* (2006.01)
(Continued)

(52) U.S. Cl.
CPC ........ *A61K 41/0061* (2013.01); *A61K 9/0014* (2013.01); *A61K 9/08* (2013.01);
(Continued)

(58) Field of Classification Search
CPC .... A61N 5/0616; A61N 5/062; A61N 5/0624; A61N 2005/0642; A61N 2005/0652;
(Continued)

(56) References Cited

U.S. PATENT DOCUMENTS 4,100,415 A 7/1978 Blaisdell et al.
4,344,256 A 8/1982 King
(Continued)

FOREIGN PATENT DOCUMENTS

AU 43869/01 A1 5/2001
BR 102014019194-1 B1 10/2022
(Continued)

OTHER PUBLICATIONS

Affidavit of Duncan Hall, Aug. 10, 2021.
(Continued)

*Primary Examiner* — Ahmed M Farah
(74) *Attorney, Agent, or Firm* — Foley & Lardner LLP

(57) ABSTRACT

A method of enhancing penetration of a topical composition of 5-aminolevulinic acid (ALA) into tissue for photodynamic therapy includes topically applying ALA to a treatment area to be treated with photodynamic therapy. The method further includes, after the ALA is applied to the treatment area, covering the treatment area with a low density polyethylene barrier. The treatment area is covered with the low density polyethylene barrier prior to light treatment to minimize transepidermal water loss from the treatment area.

6 Claims, 12 Drawing Sheets

Related U.S. Application Data division of application No. 17/487,698, filed on Sep. 28, 2021, now Pat. No. 11,571,478, which is a continuation of application No. 17/109,311, filed on Dec. 2, 2020, now Pat. No. 11,135,293, which is a continuation of application No. 16/438,702, filed on Jun. 12, 2019, now Pat. No. 11,077,192, which is a continuation of application No. 15/869,164, filed on Jan. 12, 2018, now Pat. No. 10,357,567.

(51) Int. Cl.
  *A61K 9/08* (2006.01)
  *A61K 31/75* (2006.01)
  *A61K 47/10* (2017.01)
  *A61N 5/06* (2006.01)
  *A61P 17/12* (2006.01)

(52) U.S. Cl.
  CPC .............. *A61K 31/75* (2013.01); *A61K 47/10* (2013.01); *A61N 5/062* (2013.01); *A61P 17/12* (2018.01); *A61N 2005/0633* (2013.01); *A61N 2005/0642* (2013.01); *A61N 2005/0652* (2013.01); *A61N 2005/0659* (2013.01); *A61N 2005/0663* (2013.01)

(58) Field of Classification Search
  CPC .... A61N 2005/0659; A61N 2005/0662; A61N 2005/0663; A61N 5/067; A61K 41/0057; A61K 41/0061; A61K 41/0071; A61K 41/0076; A61K 9/0014; A61K 9/08; A61K 31/745; A61K 31/75; A61K 31/765
  USPC ...................................... 607/88, 89, 96, 100
  See application file for complete search history.

(56) References Cited

U.S. PATENT DOCUMENTS

| | | | |
|---|---|---|---|
| 4,667,658 A | 5/1987 | Guibert | |
| 4,805,202 A | 2/1989 | Deucher et al. | |
| 4,823,858 A | 4/1989 | Perutz | |
| 4,832,294 A | 5/1989 | Eidem | |
| 5,032,400 A | 7/1991 | Wiersum et al. | |
| 5,079,262 A | 1/1992 | Kennedy et al. | |
| 5,209,578 A | 5/1993 | Kennedy et al. | |
| 5,211,938 A | 5/1993 | Kennedy et al. | |
| 5,441,531 A | 8/1995 | Zarate et al. | |
| 5,474,528 A | 12/1995 | Meserol | |
| 5,489,279 A | 2/1996 | Meserol | |
| 5,505,726 A | 4/1996 | Meserol | |
| 5,601,838 A | 2/1997 | Hind | |
| 5,686,065 A | 11/1997 | Haney | |
| 5,782,895 A | 7/1998 | Zarate et al. | |
| 5,814,008 A | 9/1998 | Chen et al. | |
| 5,849,027 A | 12/1998 | Gart et al. | |
| 5,856,566 A | 1/1999 | Golub | |
| 5,954,703 A | 9/1999 | Golub | |
| 6,223,071 B1 | 4/2001 | Lundahl et al. | |
| 6,231,593 B1 | 5/2001 | Meserol | |
| 6,290,713 B1 | 9/2001 | Russell | |
| 6,335,465 B1 | 1/2002 | Golub | |
| 6,559,183 B1 | 5/2003 | Schmid et al. | |
| 6,709,446 B2 | 3/2004 | Lundahl et al. | |
| 6,897,238 B2 | 5/2005 | Anderson | |
| 6,979,101 B2 | 12/2005 | Sauska et al. | |
| 7,001,413 B2 | 2/2006 | Butler | |
| 7,033,381 B1 | 4/2006 | Larsen | |
| 7,131,990 B2 | 11/2006 | Bansal et al. | |
| 7,156,865 B2 | 1/2007 | Waldmann | |
| 7,190,109 B2 | 3/2007 | Lundahl et al. | |
| 7,311,722 B2 | 12/2007 | Larsen | |
| 7,347,573 B1 | 3/2008 | Isler | |
| D613,872 S | 4/2010 | Carota et al. | |
| 7,723,910 B2 | 5/2010 | Lundahl et al. | |
| 7,730,893 B2 | 6/2010 | Dougal | |
| 8,030,836 B2 | 10/2011 | Lundahl et al. | |
| 8,216,289 B2 | 7/2012 | Lundahl et al. | |
| 8,226,289 B2 | 7/2012 | Lindeberg | |
| 8,451,601 B2 | 5/2013 | Bohn et al. | |
| 8,608,737 B2* | 12/2013 | Mehta | A61B 18/1206 606/41 |
| 8,609,073 B2 | 12/2013 | Lundahl et al. | |
| 8,638,546 B2 | 1/2014 | Hoshino | |
| 8,758,418 B2 | 6/2014 | Lundahl et al. | |
| 8,759,396 B2 | 6/2014 | Wulf et al. | |
| 8,899,791 B2 | 12/2014 | Liu | |
| 8,947,320 B2 | 2/2015 | King et al. | |
| 8,954,703 B2 | 2/2015 | Koren et al. | |
| 9,009,984 B2 | 4/2015 | Caskey et al. | |
| 9,108,045 B2 | 8/2015 | Sakamoto et al. | |
| 9,186,349 B2 | 11/2015 | Rajagopalan | |
| 9,227,082 B2 | 1/2016 | Mcdaniel | |
| 9,241,957 B2 | 1/2016 | Lundahl et al. | |
| 9,339,540 B2 | 5/2016 | Lundahl | |
| 9,387,341 B2 | 7/2016 | Lundahl | |
| D768,291 S | 10/2016 | Carota et al. | |
| 9,492,681 B2 | 11/2016 | Aydt et al. | |
| 9,533,170 B2 | 1/2017 | Dye et al. | |
| 9,561,273 B2 | 2/2017 | Epshtein | |
| 9,561,276 B2 | 2/2017 | Lundahl | |
| 9,597,150 B2 | 3/2017 | Lundahl | |
| 9,723,991 B2 | 8/2017 | Lundahl et al. | |
| 10,029,116 B2* | 7/2018 | Lundahl | A61N 5/062 |
| 10,357,567 B1 | 7/2019 | Lundahl et al. | |
| 10,589,122 B2 | 3/2020 | Boyajian et al. | |
| 10,603,508 B2 | 3/2020 | Boyajian et al. | |
| 10,688,147 B2* | 6/2020 | Garruto | A61K 36/28 |
| 10,786,571 B2 | 9/2020 | Solioz et al. | |
| 10,814,114 B2 | 10/2020 | Boyajian et al. | |
| 11,077,192 B2 | 8/2021 | Lundahl et al. | |
| 11,135,293 B2 | 10/2021 | Lundahl et al. | |
| 11,179,574 B2 | 11/2021 | Boyajian et al. | |
| 11,235,169 B1 | 2/2022 | Osterloh et al. | |
| 11,333,336 B1 | 5/2022 | Tobin et al. | |
| 11,446,512 B2 | 9/2022 | Boyajian et al. | |
| 11,697,028 B2 | 7/2023 | Boyajian et al. | |
| 2001/0021812 A1 | 9/2001 | Lundahl et al. | |
| 2002/0029071 A1 | 3/2002 | Whitehurst | |
| 2003/0088296 A1 | 5/2003 | Waldmann | |
| 2003/0105163 A1 | 6/2003 | Kennedy et al. | |
| 2003/0216795 A1 | 11/2003 | Harth et al. | |
| 2004/0010299 A1 | 1/2004 | Tolkoff et al. | |
| 2004/0068305 A1 | 4/2004 | Bansal et al. | |
| 2004/0093043 A1 | 5/2004 | Edel et al. | |
| 2004/0157905 A1 | 8/2004 | Kennedy et al. | |
| 2004/0162596 A1 | 8/2004 | Altshuler et al. | |
| 2004/0260365 A1 | 12/2004 | Groseth et al. | |
| 2005/0075703 A1 | 4/2005 | Larsen | |
| 2005/0090429 A1 | 4/2005 | Bonasera et al. | |
| 2005/0090877 A1 | 4/2005 | Harth et al. | |
| 2005/0093485 A1 | 5/2005 | Spivak | |
| 2005/0157499 A1 | 7/2005 | Kim | |
| 2006/0182790 A1 | 8/2006 | Mayoral | |
| 2006/0241726 A1 | 10/2006 | Whitehurst | |
| 2006/0253175 A1 | 11/2006 | Fan et al. | |
| 2006/0274549 A1 | 12/2006 | Fukuyoshi | |
| 2006/0287696 A1 | 12/2006 | Wright et al. | |
| 2007/0021806 A1 | 1/2007 | Mercier et al. | |
| 2007/0088410 A1 | 4/2007 | Chung et al. | |
| 2007/0283655 A1 | 12/2007 | Tobin | |
| 2008/0031924 A1 | 2/2008 | Gilson et al. | |
| 2008/0180950 A1 | 7/2008 | Kang et al. | |
| 2008/0188558 A1 | 8/2008 | Godal et al. | |
| 2009/0099499 A1 | 4/2009 | Persin et al. | |
| 2009/0177190 A1 | 7/2009 | Lee | |
| 2009/0247932 A1 | 10/2009 | Barolet | |
| 2009/0270946 A1 | 10/2009 | Spivak | |
| 2009/0324727 A1 | 12/2009 | Foguet Roca | |
| 2010/0010591 A1 | 1/2010 | Daffer | |
| 2010/0118522 A1 | 5/2010 | Hente | |
| 2010/0174222 A1 | 7/2010 | McDaniel | |

(56) References Cited

U.S. PATENT DOCUMENTS

| | | |
|---|---|---|
| 2010/0174223 A1 | 7/2010 | Sakamoto et al. |
| 2010/0298758 A1 | 11/2010 | Christiansen et al. |
| 2011/0020441 A1* | 1/2011 | Klaveness ............ A61K 9/1635 |
| | | 514/357 |
| 2011/0053965 A1 | 3/2011 | Trigiante |
| 2011/0106222 A1 | 5/2011 | Wilson et al. |
| 2011/0218597 A1 | 9/2011 | Wang |
| 2011/0224598 A1 | 9/2011 | Barolet |
| 2011/0243789 A1 | 10/2011 | Roberts |
| 2011/0270092 A1 | 11/2011 | Kang et al. |
| 2011/0293528 A1 | 12/2011 | Godal et al. |
| 2012/0004711 A1 | 1/2012 | Hilty |
| 2012/0035719 A1 | 2/2012 | Forster et al. |
| 2012/0104277 A1 | 5/2012 | Morren |
| 2012/0129879 A1 | 5/2012 | Cantrell et al. |
| 2012/0283328 A1 | 11/2012 | Modi |
| 2012/0287671 A1 | 11/2012 | Parker et al. |
| 2012/0296260 A1 | 11/2012 | Vizethum et al. |
| 2012/0303101 A1 | 11/2012 | Rogers et al. |
| 2013/0066404 A1 | 3/2013 | Tapper et al. |
| 2013/0066405 A1 | 3/2013 | Dougal |
| 2013/0102906 A1 | 4/2013 | Lundahl et al. |
| 2013/0190845 A1 | 7/2013 | Liu et al. |
| 2013/0274834 A1 | 10/2013 | Barolet et al. |
| 2013/0289089 A1 | 10/2013 | Morris et al. |
| 2013/0304019 A1 | 11/2013 | Cooper et al. |
| 2013/0315999 A1 | 11/2013 | Paithankar et al. |
| 2014/0010761 A1 | 1/2014 | Parent et al. |
| 2014/0067024 A1 | 3/2014 | Jones et al. |
| 2014/0121631 A1 | 5/2014 | Bean et al. |
| 2014/0303547 A1 | 10/2014 | Loupis et al. |
| 2015/0018751 A1 | 1/2015 | Kerber |
| 2015/0021221 A1 | 1/2015 | Hendrickson et al. |
| 2015/0162109 A1 | 6/2015 | Nager |
| 2015/0190651 A1 | 7/2015 | Jayavanth et al. |
| 2015/0217132 A1 | 8/2015 | Makkapati et al. |
| 2015/0238776 A1 | 8/2015 | Sakamoto et al. |
| 2015/0290028 A1 | 10/2015 | Isserow et al. |
| 2015/0290470 A1 | 10/2015 | Tapper et al. |
| 2016/0008623 A1 | 1/2016 | Jones et al. |
| 2016/0030565 A1 | 2/2016 | Wulf et al. |
| 2016/0045015 A1 | 2/2016 | Baldwin |
| 2016/0045757 A1 | 2/2016 | Groseth |
| 2016/0051832 A1 | 2/2016 | Mordon |
| 2016/0166846 A1 | 6/2016 | Chae |
| 2016/0175608 A1 | 6/2016 | Livingston |
| 2016/0175609 A1 | 6/2016 | Dye et al. |
| 2016/0175610 A1 | 6/2016 | Livingston et al. |
| 2016/0255941 A1 | 9/2016 | Yang et al. |
| 2016/0317831 A1 | 11/2016 | Lundahl |
| 2016/0346392 A1 | 12/2016 | Wulf |
| 2017/0106205 A1 | 4/2017 | Boyajian et al. |
| 2017/0157379 A1 | 6/2017 | Boyajian et al. |
| 2017/0216616 A1 | 8/2017 | Boyajian et al. |
| 2018/0043178 A1 | 2/2018 | Iguchi et al. |
| 2018/0178034 A1 | 6/2018 | Iguchi et al. |
| 2018/0311507 A1 | 11/2018 | Barolet |
| 2018/0344852 A1 | 12/2018 | Solioz et al. |
| 2019/0105261 A1* | 4/2019 | Waugh ................ A61K 8/735 |
| 2019/0290763 A1 | 9/2019 | Lundahl et al. |
| 2020/0010997 A1 | 1/2020 | Kwon |
| 2020/0100997 A1 | 4/2020 | Soler et al. |
| 2020/0246630 A1 | 8/2020 | Boyajian et al. |
| 2020/0261580 A1* | 8/2020 | Willey .................. A61K 9/06 |
| 2020/0269063 A1 | 8/2020 | Boyajian et al. |
| 2020/0398071 A1 | 12/2020 | Boyajian et al. |
| 2021/0085788 A1 | 3/2021 | Lundahl et al. |
| 2022/0008538 A1 | 1/2022 | Lundahl et al. |
| 2022/0040494 A1* | 2/2022 | Boyajian ............ A61N 5/0616 |
| 2022/0354952 A1 | 11/2022 | Willey |
| 2023/0131170 A1 | 4/2023 | Sanghvi et al. |
| 2024/0335360 A1 | 10/2024 | Foguet et al. |
| 2024/0335380 A1 | 10/2024 | Foguet et al. |

FOREIGN PATENT DOCUMENTS

| | | | |
|---|---|---|---|
| CA | 2706642 C | 8/2002 | |
| CA | 2568744 A1 | 12/2005 | |
| CA | 2738861 A1 | 7/2011 | |
| CN | 1941799 A | 4/2007 | |
| CN | 103043330 A | 4/2013 | |
| CN | 203097540 U | 7/2013 | |
| CN | 206822964 U | 1/2018 | |
| DE | 69827286 T2 | 11/2005 | |
| EP | 1 162 400 A2 | 12/2001 | |
| EP | 1238652 A1 * | 9/2002 | ........... A61K 31/197 |
| EP | 1 311 259 B1 | 5/2003 | |
| EP | 2 456 382 B1 | 5/2012 | |
| FR | 2813747 A | 3/2002 | |
| JP | S49-002185 | 1/1974 | |
| JP | 326327 B2 | 4/1991 | |
| JP | H04-500770 A | 2/1992 | |
| JP | 2524147 B2 | 8/1996 | |
| JP | 3262327 B2 | 3/1998 | |
| JP | 2736475 B2 | 4/1998 | |
| JP | H11-239624 A | 9/1999 | |
| JP | 2000-177155 A | 6/2000 | |
| JP | 2002-529495 A | 9/2002 | |
| JP | 2006-511275 A | 4/2006 | |
| JP | 2006-519047 A | 8/2006 | |
| JP | 2009-055969 A | 3/2009 | |
| JP | 2010-513363 | 4/2010 | |
| JP | 2010-515714 A | 5/2010 | |
| JP | 2010-212819 A | 9/2010 | |
| JP | 4855775 B2 | 1/2012 | |
| JP | 2013-019237 A | 1/2013 | |
| JP | 2014-067529 A | 4/2014 | |
| JP | 2019-123708 A1 | 7/2019 | |
| KR | 20070063718 A | 6/2007 | |
| KR | 20090005028 A | 1/2009 | |
| KR | 20090055891 A | 6/2009 | |
| KR | 101180416 B1 | 9/2012 | |
| KR | 20120100861 A | 9/2012 | |
| KR | 101237952 B1 | 2/2013 | |
| KR | 101244434 B1 | 3/2013 | |
| KR | 101576623 B1 | 12/2015 | |
| WO | WO-87/07321 A1 | 12/1987 | |
| WO | WO-93/09847 A1 | 5/1993 | |
| WO | WO-95/07077 A1 | 9/1993 | |
| WO | WO-96/06602 A1 | 3/1996 | |
| WO | WO-97/15226 A1 | 5/1997 | |
| WO | WO-99/22802 A1 | 5/1999 | |
| WO | WO-99/56827 A2 | 11/1999 | |
| WO | WO-00/41726 A2 | 7/2000 | |
| WO | WO-02/13788 A1 | 2/2002 | |
| WO | WO-02/30512 A1 | 4/2002 | |
| WO | WO-02/062420 A1 | 8/2002 | |
| WO | WO-02/098508 A1 | 12/2002 | |
| WO | WO-2005/030328 A2 | 4/2005 | |
| WO | WO-2006/013390 A1 | 2/2006 | |
| WO | WO-2007/090256 A1 | 8/2007 | |
| WO | WO-2007/112427 A2 | 10/2007 | |
| WO | WO-2009/003173 A1 | 12/2008 | |
| WO | WO-2009/131727 A2 | 10/2009 | |
| WO | WO-2010/044879 A2 | 4/2010 | |
| WO | WO-2010/128751 A2 | 11/2010 | |
| WO | WO-2011/084722 A1 | 7/2011 | |
| WO | WO-2011/124912 A1 | 10/2011 | |
| WO | WO-2011/153599 A1 | 12/2011 | |
| WO | WO-2012/086991 A2 | 6/2012 | |
| WO | WO-2013/110021 A1 | 7/2013 | |
| WO | WO-2014/064075 A1 | 5/2014 | |
| WO | WO-2014/131115 A1 | 9/2014 | |
| WO | WO-2014/147624 A1 | 9/2014 | |
| WO | WO-2015/041919 A1 | 3/2015 | |
| WO | WO-2017/066270 A1 | 4/2017 | |
| WO | WO-2019/018408 A1 | 1/2019 | |
| WO | WO-2023/067519 A1 | 4/2023 | |

(56) References Cited

FOREIGN PATENT DOCUMENTS

| WO | WO-2024/209064 A1 | 10/2024 |
|---|---|---|
| WO | WO-2024/209073 A1 | 10/2024 |

OTHER PUBLICATIONS

Agostinis et al. Photodynamic therapy of cancer: an update. CA: A Cancer Journal for Clinicians. May 2011; 61(4):250-2.
Aktilite CL128 Operators Manual with Metvixia, Revised Jun. 2008.
Ameluz, Prescribing Information (May 2016).
Ang et al., "Photodynamic Therapy and Pain: A Systematic Review", Photodiagnosis and Photodynamic Therapy 19 (Jul. 2017) 308-344.
Apalla, Z. et al., Skin Cancer: Preventive Photo dynamic Therapy in Patients With Face and Scalp Cancerization. A Randomized Placebo-Controlled Study, British Journal of Dermatology, Jan. 2010, 162, pp. 171-175.
Barolet, D. et al., Radiant Near Infrared Light Emitting Diode Exposure as Skin Preparation to Enhance Photodynamic Therapy Inflammatory Type Acne Treatment Outcome, Lasers in Surgery and Medicine vol. 42, No. 2, Feb. 1, 2010, pp. 171-178.
Berardesca E, Vignoli GP, Fideli D, Maibach H. Effect of occlusive dressings on the stratum corneum water holding capacity. The American Journal of the Medical Sciences. Jul. 1992; 304(1):25-28.
Bissonnette R. Photodynamic therapy. In: Gold M.H., editor. Photodynamic Therapy in Dermatology. Springer Science and Business Media, LLC; New York, NY, USA: Apr. 2011. pp. 221-229.
Blu-U, Operating Manual (2006).
Braathan, Lasse R., et al. "Guidelines on the Use of Photodynamic Therapy for Nonmelanoma Skin Cancer: an International Consensus." Journal of the American Academy of Dermatology 56.1, Jan. 2007, pp. 125-143.
Calderhead RG. Light-emitting diode phototherapy in dermatological practice in lasers in dermatology and medicine. Lasers in Dermatology and Medicine. Aug. 2011:231-265.
Champeau et al. "Photodynamic therapy for skin cancer: How to enhance drug penetration?", Journal of Photochemistry and Photobiology B: Biology, vol. 197, Jul. 2, 2019.
David M. et al., Psoriasis Therapy: Comparative Studies With A Hydrocolloid Dressing, Plastic Film Occlusion, And Triamcinolone Acetonide Cream, Journal of the American Academy of Dermatology, Sep. 1989, 21, pp. 511-514.
Declaration of Dr. Howard Rogers MD, Ph.D, Oct. 19, 2021.
Dermatology Times, Warming the Skin During PDT Incubation Period Boosts Porphyrin Synthesis, Apr. 1, 2013, 3 pages.
Dragieva, G. et al., "A Randomized Controlled Clinical Trial of Topical Photodynamic Therapy with Methyl Aminolaevulinate in the Treatment of Actinic Keratoses in Transplant Recipients." British Journal of Dermatology 151.1, Jul. 2004, pp. 196-200.
DUSA Levulan Press Release, Dec. 6, 1999.
Dusa Pharmaceuticals, Inc., Levulan PDT Versus Vehicle for Extremity Actinic Keratoses (AK), U.S. National Library of Medicine, ClinicalTrials.gov, First Posted Oct. 25, 2011, Last Update Posted Mar. 14, 2013, 80 pgs.
Dusa Pharmaceuticals, Inc., Maximal Use Systemic Exposure (MUSE) Study of Levulan Kerastick, U.S. National Library of Medicine, ClinicalTrials.gov, First Posted Nov. 3, 2014, Last Update Posted Jan. 13, 2017, 68 pgs.
Dusa Pharmaceuticals, Inc., Maximal Use Systemic Exposure Study of Levulan Kerastick (MUSE 2), U.S. National Library of Medicine, ClinicalTrials.gov, First Posted Dec. 11, 2015, Last Update Posted Sep. 18, 2017, 69 pgs.
Dusa Pharmaceuticals, Inc., Safety and Efficacy Study of Photodynamic Therapy With Levulan Kerastick Blue Light for Actinic Keratoses on the Upper Extremities, U.S. National Library of Medicine, ClinicalTrials.gov, First Posted May 14, 2014, Last Update Posted Sep. 16, 2015, 112 pgs.
Dusa Pharmaceuticals, Inc., Short-Incubation Levulan Photodynamic Therapy Versus Vehicle for Face/Scalp Actinic Keratosis (AK), U.S. National Library of Medicine, ClinicalTrials.gov, First Posted Nov. 22, 2011, Last Update Posted Oct. 28, 2016, 184 pgs.
Encyclopedia Britannica, "Gel: Physics and Chemistry", 4 pages, Jul. 20, 1998, and "Gel: Additional Information", 1 page, Available on line at: https://www.britannica.com/science/gel and https://www.britannica.com/science/gel/additional-info#history.
European Medicines Agency CHMP Assessment Report (excerpts), Oct. 20, 2011.
Farber, E.M. et al., Therapy Of Mycosis Fungoides With Topically Applied Fluocinolone Acetonide Under Occlusive Dressing, Cancer, Feb. 1966, vol. 19(2), pp. 237-245.
Fauteck, Europe PMC Website Database Listing, Oct. 25, 2007.
Fauteck JD, Ackermann G, Birkel M, Breuer M, Moor AC, Ebeling A, Ortland C. Fluorescence characteristics and pharmacokinetic properties of a novel self-adhesive 5-ALA patch for photodynamic therapy of actinic keratoses, Feb. 2008.
Fehr et al., Photodynamic Therapy of Vulvar and Vaginal Condyloma and Intraepithelial Neoplasia Using Topically Applied 5-Aminolevulinic Acid, Lasers in Surgery and Medicine, Mar. 2002, 30:273-279, 7 pages.
Fehr et al., Selective Photosensitizer Distribution in Vulvar Condyloma Acuminatum After Topical Application of 5-Aminolevulinic Acid, Am. J. Obstet. Gynecol., vol. 174(3), Mar. 1996, pp. 951-957.
Frank, Lawrence et al., Flurandrenolone And Occlusion In Psoriasis: Prolonged Topical Treatment, Arch Dermatol, Mar. 1964, vol. 89(3), pp. 404-410.
Fry, L. et al., Effect Of Plastic Occlusive Dressings On Psoriatic Epidermis, Br. J. Dermatol, May 1970, 82, pp. 458-462.
Galitzer, B. I., Effect Of Retinoid Pretreatment On Outcomes Of Patients Treated By Photodynamic Therapy For Actinic Keratosis Of The Hand And Forearm, Journal of Drugs in Dermatology, Oct. 2011, vol. 10, Issue 10, pp. 1124-1132.
GLAD.com.au: "GLAD History", 2012, [online] URL: http://www.glad.com.au/about-glad/glad-history/, retrieved online Nov. 8, 2019.
Harris DR. Percutaneous absorption and the surface area of occluded skin: a scanning electron microscopic study. British Journal of Dermatology. Jul. 1974; 91(27-32).
Hongcharu W., Taylor C., Chang, Y., Aghasi, D., Suthamjariya, K., Anderson, R. Topical ALA-photodynamic therapy for the treatment of acne vulgaris. J Invest Dermatol. Aug. 2000;115(2):183-92.
Hurlimann et al., Photodynamic Therapy of Superficial Basal Cell Carcinomas Using Topical 5-Aminolevulinic Acid in a Nanocolloid Lotion, Pharmacology and Treatment, Dermatology 197, Apr. 1998, pp. 248-254.
International Patent Reviews, LLC review of U.S. Pat. No. 10,357,567 dated Jul. 26, 2021.
Jeffes E., Mccullough J., Weinstein G., Fergin P., Nelson J., Shull T., Simpson K., Bukaty L., Hoffman W., Fong N. Photodynamic therapy of actinic keratosis with topical 5-aminolevulinic acid. A pilot dose-ranging study. Arch Dermatol. Jun. 1997.
Juzenas, P. et al., Uptake of Topically Applied 5-Aminolevulinic Acid and Production of Protoporphyrin IX in Normal Mouse Skin: Dependence on Skin Temperature, Photochemistry and photobiology, vol. 69, No. 4, Apr. 1, 1999, pp. 478-481.
Kim et al. "In vivo skin absorption dynamics of topically applied pharmaceuticals monitored by fiber-optic diffuse reflectance spectroscopy" Spectrochimica Acta Part A 66, Mar. 2007, 768-772.
Kurwa, H. et al., "A Randomized Paired Comparison of Photodynamic Therapy and Topical 5-Fluorouracil in the Treatment of Actinic Keratoses." Journal of the American Academy of Dermatology 41.3, Sep. 1999, pp. 414-418.
Letter to UVBiotek, LLC dated Jul. 28, 2017 Re: K170187, Trade/Device Name: Photodynamic Therapy Device, available at https://www.accessdata.fda.gov/cdrh_docs/pdf17/K170187.pdf (accessed Apr. 30, 2020).
Levulan, Label (Dec. 2009).
Levulan, Label (Mar. 2002).
MacCormack, M.A., "Photodynamic Therapy in Dermatology: An Update on Applications and Outcomes." Seminars in Cutaneous Medicine and Surgery. vol. 27, No. 1, WB Saunders, Mar. 2008, pp. 52-62.
Maisch et al., "Fluorescence Induction of Protoporphyrin IX by a New 5-Aminolevulinic Acid Nanoemulsion Used for Photodynamic

(56) References Cited

OTHER PUBLICATIONS

Therapy in a Full-Thickness ex vivo Skin Model," Experimental Dermatology, 19, Oct. 2009, ebook p. e302-e305.
Matsumara H. et al., Effect Of Occlusion On Human Skin, Contact Dermatitis, Oct. 1995, 33, pp. 231-235.
McLaren G. Photodynamic therapy. In; Pfenninger and Fowler's procedures for primary care. Third Ed. Mosby Elsevier; Philadelphia, PA: (c) 2011. pp 397-400 (eBook published Sep. 2010).
Mordon, A Commentary on the Role of Skin Temperature on the Effectiveness of ALA-PDT in Dermatology, Photodiagnosis and Photodynamic Therapy, Sep. 2014.
National Association of Container Distributors, The Definitive Guide to Plastics for the Packaging Industry, available at https://www.nacd.net/pdf/07102015_NACD_GuideToPlastics_1-1.pdf (pdf creation date Jul. 15, 2015, last accessed Sep. 8, 2018).
News article entitled DUSA Pharmaceuticals To Pay U.S. $20.75 Million To Settle False Claims Act Allegations Relating To Promotion Of Unsupported Drug Administration Process, Aug. 24, 2020.
Nishimura et al., "Iontophoretic Photosensitization of the Skin Re-evaluated by Colorimetric Imaging in Senile Patients." Bioimages 19, 1-6, accepted Jan. 2011.
Nucci et al., Treatment of Anogenital Condylomata Acuminata with Topical Photodynamic Therapy: Report of 14 Cases and Review, International Journal of Infectious Diseases, 14S, Sep. 2010, pp. e280-e282.
Ozog, D.M. et al., "Photodynamic Therapy: A Clinical Consensus Guide." Dermatologic Surgery 42.7, Jul. 2016, pp. 804-827.
Palm M., Goldman PM. Aminolevulinic acid: actinic keratosis and photorejuvenation. In: Gold M.H., editor. Photodynamic Therapy in Dermatology. Springer Science and Business Media, LLC. Nov. 2011:5-30.
Pariser, David M. et al., Randomized Vehicle-Controlled Study of short Drug Incubation Aminolevulinic Acid Photodynamic Therapy for Actinic Keratoses of the Face or Scalp, American Society for Dermatologic Surgery, Inc., Mar. 2016, pp. 296-304.
Petition for Inter Partes Review Under 35 U.S.C. 312, Oct. 19, 2021.
Reinhold et al., A Randomized, Double-Blind, Phase III, Multicentre Study to Evaluate the Safety and Efficacy of BF-200 ALA (Ameluz®) vs. Placebo in the Field-Directed Treatment of Mild-to-Moderate Actinic Keratosis with Photodynamic Therapy (PDT) When Using the BF-RhodoLED® Lamp, British Journal of Dermatology, 175(4): 696-705, Feb. 27, 2016, 10 pages.
Rick K, Sroka R, Stepp H, Kriegmair M, Huber RM, Jacob K, Baumgartner R. Pharmacokinetics of 5-aminolevulinic acidinduced protoporphyrin IX in skin and blood. J Photochem Photobiol B. Oct. 1997;40(3):313-9.
Robertson, G., Food Packaging Principles and Practice, excerpt from Chapter 2.3.6.1, 3rd Ed., 2013, CRC Press: Boca Raton, FL, 11 pages.
Sakamoto FH, Torezan L, Anderson RR. Photodynamic therapy for acne vulgaris: a critical review from basics to clinical practice: part II. Understanding parameters for acne treatment with photodynamic therapy. J Am Acad Dermatol. Aug. 2010;63(2):195-211.
Schmieder, G. et al., A Multicenter, Randomized, Vehicle-Controlled Phase 2 Study of Blue Light Photodynamic Therapy With Aminolevulinic Acid HCl 20% Topical Solution for the Treatment of Actinic Keratoses on the Upper Extremities: The Effect of Occlusion During the Drug Incubation Period, Journal of Drugs in Dermatology, vol. 11, Issue 12, Dec. 2012, pp. 1483-1489.
Sotiriou E, Apalla Z, Maliamani F, Zaparas N, Panagiotidou D, Ioannides D. Intraindividual, right-left comparison of topical 5-aminolevulinic acid photodynamic therapy vs. 5% imiquimod cream for actinic keratoses on the upper extremities, Feb. 2009.
Sotiriou Pubmed Website Database Listing, Sep. 23, 2009.
Sulzberger et al., Thin Pliable Plastic Films in Topical Dermatologic Therapy, Arch Dermatol, Dec. 1961, 84(6), pp. 1027-1028.
Taub et al., A Randomized, Blinded, Bilateral Intraindividual, Vehicle-Controlled Trial Of The Use Of Photodynamic Therapy With 5-Aminolevulinic Acid And Blue Light For The Treatment Of Actinic Keratoses Of The Upper Extremities, Journal of Drugs in Dermatology, Sep. 2011, vol. 10, Issue 9, pp. 1049-1056.
Third Party Submission filed in U.S. Appl. No. 17/109,311, filed Jun. 21, 2021, 21 pages.
Tosti, A. et al., Clobetasol Propionate 0.05 % Under Occlusion In The Treatment Of Alopecia Totalis/Universalis, J. Am Acad Dermatol, Jul. 2003, vol. 49, No. 1, pp. 96-98.
Van Den Akker et al., Effect of Elevating the Skin Temperature During Topical ALA Application on in vitro ALA penetration Through Mouse Skin and in vivo PpIX production in Human Skin, Photochemical and Photobiological Sciences, Royal Society of Chemistry, Cambridge, GB, vol. 3, No. 3, Mar. 1, 2004, pp. 263-267.
Wachowska et al., Aminolevulinic acid (ALA) as a prodrug in photodynamic therapy of cancer. Molecules. May 2011; 16(5): 4140-4164.
Warren et al., "Pain Associated with Aminolevulinic Acid-Photodynamic Therapy of Skin Disease", J Am Acad Dermatol. Dec. 2009; 61(6): 1033-1043.
Webpage printout, Hill Laboratories Company, "Aklarus Phototherapy Treatment System with Red, Blue and Infrared Wavelengths by Hill Therapeutics," available at https://hilllabs.com/therapeutics/Aklarus-Photo-Therapy-System.php (accessed Apr. 30, 2020).
Willey et al., "Temperature-Modulated Photodynamic Therapy for the Treatment of Actinic Keratosis on the Extremities: A Pilot Study," Dermatol Surg; 40: 1094-1102, Oct. 1, 2014.
Willey et al., American Society for Laser Medicine and Surgery Abstracts, #147, Ultra Fast Thermal PDT for Facial AKs: Proof of Concept Study, Mar. 2017, 2 pages.
Willey Pubmed Website Database Listing, Oct. 2014.
Willey et al., Abstract of Temperature-Modulated Photodynamic Therapy for the Treatment of Actinic Keratosis on the Extremities: A Pilot Study, Dermatol Surg., 40 (10), Oct. 2014, 2 pages, https://www.ncbi.nlm.nih.gov/pubmed/25207759.
Willey, Introducing the New Red Light ALA PDT, Feb. 15, 2017, 3 pages, https://andreawilleymd.com/the-new-red-light-ala-pdt/.
Wolf P., Rieger E. and Kerl H. Topical photodynamic therapy with endogenous porphyrins after application of 5-aminolevulinic acid: an alternative treatment modality for solar keratoses, superficial squamous cell carcinomas, and basal cell carcinomas?, Jan. 1993.
Ye et al. "Evaluation of Hydrogel Suppositories for Delivery of 5-Aminolevulinic Acid and Hematoporphyrin Monomethyl Ether to Rectal Tumors," Molecules, Oct. 2016, 21, 1347, 1-12.
Zackheim, H. et al., Topical Corticosteroids for Mycosis Fungoides, Experience in 79 Patients, Arch Dermatol, Aug. 1998, vol. 134, pp. 949-954.
Zhang et al., "Topical 5-Aminolevulinic Photodynamic Therapy with Red Light vs Intense Pulsed Light for the Treatment of Acne Vulgaris _ A Spilit [sic] Face, Randomized, Prospective Study," Dermato-Endocrinology, Oct. 2017, vol. 9, No. 1, e1375634 (9 pages).
Agostinis, P., et al. (2011), "Photodynamic Therapy of Cancer: An Update", CA: A Cancer Journal for Clinicians, vol. 61(4) (Jul.-Aug. 2011), 250-281, https://doi.org/10.3322/caac.20114.
Allison, Ron R. et al., "The future of photodynamic therapy in oncology"; Future Oncol, vol. 2, No. 1; Feb. 2006; pp. 53-71.
Avci, Pinar et al., "Low-level laser (light) therapy (LLT) in skin: stimulating, healing, restoring"; Semin Cutan Med Surg., vol. 32, No. 1; Mar. 2013; pp. 41-52.
Barolet, Daniel, "Light-Emitting Diodes (LEDs) in Dermatology"; Seminars in Cutaneous Medicine and Surgery, vol. 27, No. 4; Dec. 2008; pp. 227-238.
Bourget, C. Michael, "An Introduction to Light-emitting Diodes"; HortScience, vol. 43, No. 7; Dec. 2008; pp. 1944-1946.
Brancaleon, L. et al., "Laser and Non-Laser Light Sources for Photodynamic Therapy"; Lasers Med. Sci., vol. 17, No. 3; Feb. 2002; pp. 173-186.
Calderhead, R. Glen, "The Photobiological Basics Behind Light-Emitting Diode (LED) Phototherapy"; Laser Therapy, vol. 16, No. 2; Jan. 2007; pp. 97-108.

(56) References Cited

OTHER PUBLICATIONS

Chen, Hsi-Chao et al., "Investigation of illumination efficiency on the LED therapy with different array types"; Proceedings of SPIE—The International Society for Optical Engineering, vol. 7422; Aug. 2009; 8 pages.
Finlayson, Louise et al., "Depth Penetration of Light into Skin as a Function of Wavelength from 200 to 1000 nm"; Photochemistry and Photobiology, vol. 98, No. 4; Nov. 2021; pp. 974-981.
Full Prescribing Information of Levulan—Kerastick, Mar. 2010.
Gold, Michael H. et al., "5-Aminolevulinic Acid Photodynamic Therapy: Where We Have Been and Where We Are Going"; Dermatol. Surg., vol. 30, No. 8; Aug. 2004; pp. 1077-1084.
Gold, Michael H., "Acne vulgaris: lasers, light sources and photodynamic therapy—an update 2007"; Expert Rev. Anti Infect. Ther., vol. 5, No. 6; Dec. 2007; pp. 1059-1069.
Gold, Michael H., "Therapeutic and Aesthetic Uses of Photodynamic Therapy: Part one of a five-part series: The Use of Photodynamic Therapy in the Treatment of Actinic Keratoses and in Photorejuvenation"; Journal of Clinical and Aesthetic Dermatology, vol. 1, No. 2; Jul. 2008; pp. 32-37.
Gold, Michael H., "Therapeutic and Aesthetic Uses of Photodynamic Therapy: Part two of a five-part series: Lasers and Light Treatments for Acne Vulgaris: Promising Therapies"; Journal of Clinical and Aesthetic Dermatology, vol. 1, No. 3; Sep. 2008; pp. 28-34.
Gold, Michael H., "Therapeutic and Aesthetic Uses of Photodynamic Therapy: Part three of a five-part series: Chemoprevention utilizing ALA-PDT", Journal of Clinical and Aesthetic Dermatology, vol. 1, No. 4; Nov. 2008; pp. 26-32.
Gold, Michael H., "Therapeutic and Aesthetic Uses of Photodynamic Therapy: Part four of a five-part series: ALA-PDT in Clinical Practice: How One Clinician Performs This Procedure"; Journal of Clinical and Aesthetic Dermatology, vol. 2, No. 1; Jan. 2009; pp. 32-35.
Gold, Michael H., "Therapeutic and Aesthetic Uses of Photodynamic Therapy: Part five of a five-part series: ALA-PDT and MAL-PDT: What Makes Them Different"; Journal of Clinical and Aesthetic Dermatology, vol. 2, No. 2; Feb. 2009; pp. 44-47.
Hino, Hitoshi et al., "5-Aminolevulinic acid-mediated photodynamic therapy using light-emitting diodes of different wavelengths in a mouse model of peritoneally disseminated gastric cancer"; Journal of Surgical Research, vol. 185; Jun. 2013; pp. 119-126.
Juzeniene, Asta et al., "Effectiveness of different light sources for 5-aminolevulinic acid photodynamic therapy"; Lasers in Medical Science, vol. 19; Oct. 2004; pp. 139-149.
Kalisiak, Michal S. et al., "Photodynamic Therapy for Actinic Keratoses"; Dermatol. Clin., vol. 25, No. 1; Jan. 2007; pp. 15-23.
Kernel Medical Equipment Co., Ltd, "PDT Led Light Therapy Machine For skin rejuvenation KN-7000A," © 2018, accessed at https://www.kernelmedint.com/product/pdt-led-light-therapy-machine-for-skin-rejuvenation-kn-7000a on Nov. 13, 2024.
Ko, Dong-Yeob et al., "Comparative Study of Photodynamic Therapy with Topical Methyl Aminolevulinate versus 5-Aminolevulininc Acid for Facial Actinic Keratosis with Long-Term Follow-Up"; Ann. Dermatol., vol. 26, No. 3; Jun. 2014; pp. 321-331.
Langmack, Keith et al., "Topical photodynamic therapy at low fluence rates—theory and practice"; Journal of Photochemistry and Photobiology B: Biology, vol. 60, No. 1; Apr. 2001; pp. 37-43.
Levulan—kerastick-aminolevulinic acid hydrochloride, FDA Label, 2000, 2003, 2009, 2010.
Ma, Li et al.; "Low-dose topical 5-aminolevulinic acid photodynamic therapy in the treatment of different severity of acne vulgaris"; Photodiagnosis and Photodynamic Therapy, vol. 10, No. 4; Dec. 2013, pp. 583-590.
Marrero, Allison et al., "Aminolevulinic Acid-Photodynamic Therapy Combined with Topically Applied Vascular Disrupting Agent Vadimezan Led to Enhanced Antitumor Responses"; Photochem. Photobiol., vol. 87, No. 4; Jul. 2011; pp. 910-919.
Matthews, Y.I. et al., "Topical photodynamic therapy is immunosuppressive in humans"; British Journal of Dermatology, vol. 162, No. 3; Mar. 2010; pp. 637-641.

Metvixia methyl aminolevulinate cream, 16.8%; FDA Label; Jun. 2008.
Moan, Johan et al., "The Temperature Dependence of Protoporphyrin IX Production in Cells and Tissues"; Photochemistry and Photobiology, vol. 70, No. 4; Oct. 1999; pp. 669-673.
Moseley, Harry, "Light distribution and calibration of commercial PDT LED arrays"; Photochem. Photobiol. Sci., vol. 4; Sep. 2005; pp. 911-914.
Ndjiongue, Alain Richard et al., "Visible Light Communications (VLC) Technology"; Wiley Encyclopedia of Electrical and Electronics Engineering, J.G. Webster (Ed.); https://doi.org/10.1002/047134608X.W8267; Jun. 2015; 24 pages.
Omnilux Blue Light Acne Treatment Brisbane & Gold Coast, Beauty by Laser; YouTube Video, https://www.youtube.com/watch?v=V8F-R-pw16Y; May 31, 2011; 2 pages.
Omnilux Red Light Treatment, Brisbane & Gold Coast, Beauty by Laser; YouTube Video; http://www.youtube.com/watch?v=C2f5Sn45aeQ; Oct. 29, 2008; 2 pages.
Peng, Qian et al.; "5-Aminolevulinic Acid-Based Photodynamic Therapy: Clinical Research and Future Challenges"; Cancer, vol. 79, No. 12; Jun. 1997; pp. 2282-2308.
Specimen for Beautylight, United States Trademark Serial No. 78214595, MDE Medizintechnik GmbH, Specimen submitted May 29, 2007.
Tao, Shi-qin et al.; "Low-Dose Topical 5-Aminolevulinic Acid Photodynamic Therapy in the Treatment of Different Severity of Acne Vulgaris"; Cell Biochem. Biophys., vol. 73; May 27, 2015; pp. 701-706.
Wan, Marilyn T. et al.; "Current evidence and applications of photodynamic therapy in dermatology"; Clinical, Cosmetic and Investigational Dermatology, vol. 7, May 2014; pp. 145-163.
Wang, Xiu-Li et al.; "Topical ALA PDT for the treatment of severe acne vulgaris", Photodiagnosis and Photodynamic Therapy, vol. 7; Feb. 2010; pp. 33-38.
Wilson, Brian C. et al., "The physics, biophysics and technology of photodynamic therapy"; Phys. Med. Biol., vol. 53; Apr. 2008; R61-R109.
"About Actinic Keratosis (Keratoses)"; SOMA Skin & Laser; https://somalaser.com/skin-conditions/actinic-keratosis/; accessed Nov. 21, 2024; 2 pages, referenced in Patent Owner Preliminary Response in IPR2024-01312 dated Nov. 27, 2024.
"BLU-U—Blue Light for Acne and Actinic Keratosis"; SOMA Skin & Laser; https://somalaser.com/blu-for-acne, accessed Nov. 21, 2024; 2 pages, referenced in Patent Owner Preliminary Response in IPR2024-01312 dated Nov. 27, 2024.
"How Levulan Kerastick BLU-U Works"; How It Works—Levulan Kerastick (aminolevulinic acid HCI) BLU-U; https://www.levulanhcp.com/how-it-works; accessed Nov. 21, 2024; 4 pages, referenced in Patent Owner Preliminary Response in IPR2024-01312 dated Nov. 27, 2024.
"How much space does a BLU-U require?"; Levulan Kerastick (aminolevulinic acid HCI) for Topical Solution, 20%; https://www.mydrugrep.com/mobile-campaigns/Levulan_V13a_01a/space_requirements.html; accessed Nov. 21, 2024; 3 pages, referenced in Patent Owner Preliminary Response in IPR2024-01312 dated Nov. 27, 2024.
"How to Use Levulan Kerastick BLU-U"; How To Use—Levulan Kerastick (aminolevulinic acid HCI) BLU-U; https://www.levulanhcp.com/how-to-use; accessed on Nov. 25, 2024; 6 pages, referenced in Patent Owner Preliminary Response in IPR2024-01312 dated Nov. 27, 2024.
"Photodynamic Therapy for Acne"; SOMA Skin & Laser; https://somalaser.com/photodynamic-therapy/; accessed Nov. 21, 2024; 1 page, referenced in Patent Owner Preliminary Response in IPR2024-01312 dated Nov. 27, 2024.
"Photodynamic Therapy for Actinic Keratoses and Skin Cancer"; SOMA Skin & Laser; https://somalaser.com/photodynamic-therapy-for-actinic-keratoses-and-skin-cancer/; accessed Nov. 21, 2024; 2 pages, referenced in Patent Owner Preliminary Response in IPR2024-01312 dated Nov. 27, 2024.

(56) References Cited

OTHER PUBLICATIONS

"Photodynamic Therapy for Skin Conditions"; SOMA Skin & Laser; https://www.somalaser.com/photodynamic-therapy-for-skin-conditions/; accessed Nov. 21, 2024; 4 pages, referenced in Patent Owner Preliminary Response in IPR2024-01312 dated Nov. 27, 2024.

"Photodynamic Therapy"; Photodynamic Therapy (PDT)—Dr. Heather Roberts; https://www.drheatherroberts.com/procedures-and-treatments/photodynamic-therapy-pdt-for-skin-cancer/; accessed Nov. 21, 2024; 3 pages, referenced in Patent Owner Preliminary Response in IPR2024-01312 dated Nov. 27, 2024.

"Proven Results"; Proven Results for Levulan Kerastick (aminolevulinic acid HCl) BLU-U; https://www.levulanhcp.com/efficacy#isi-homepage-levulan-hcp; accessed Nov. 25, 2024; 4 pages, referenced in Patent Owner Preliminary Response in IPR2024-01312 dated Nov. 27, 2024.

"Strike AKs with Confidence"; Levulan Kerastick (aminolevulinic acid HCl) BLU-U—HCP Home Page; https://www.levulanhcp.com/; accessed on Nov. 25, 2024; 4 pages, referenced in Patent Owner Preliminary Response in IPR2024-01312 dated Nov. 27, 2024.

"The Treatment Landscape"; Treatment Landscape—Levulan Kerastick (aminolevulinic acid HCl) BLU-U; https://www.levulanhcp.com/treatment-landscape; accessed Nov. 21, 2024; 5 pages, referenced in Patent Owner Preliminary Response in IPR2024-01312 dated Nov. 27, 2024.

"Treat What Happened Yesterday, Today"; Levulan Kerastick BLU-U; Jan. 2021; 16 pages, referenced in Patent Owner Preliminary Response in IPR2024-01312 dated Nov. 27, 2024.

Lighting-Gallery.net; My lights/completely clear/uncoated Sylvania 28W T5 HE demonstration tube; https://www.lighting-gallery.net/gallery/displayimage.php?album=1601&pos=188&pid=211863; accessed on Oct. 30, 2024; 3 pages, referenced in Patent Owner Preliminary Response in IPR2024-01312 dated Nov. 27, 2024.

Pileri, Alessandro et al.; "Photodynamic therapy: An option in mycosis fungoides"; Photodiagnosis and Photodynamic Therapy, vol. 20; Sep. 7, 2017; pp. 107-110.

\* cited by examiner

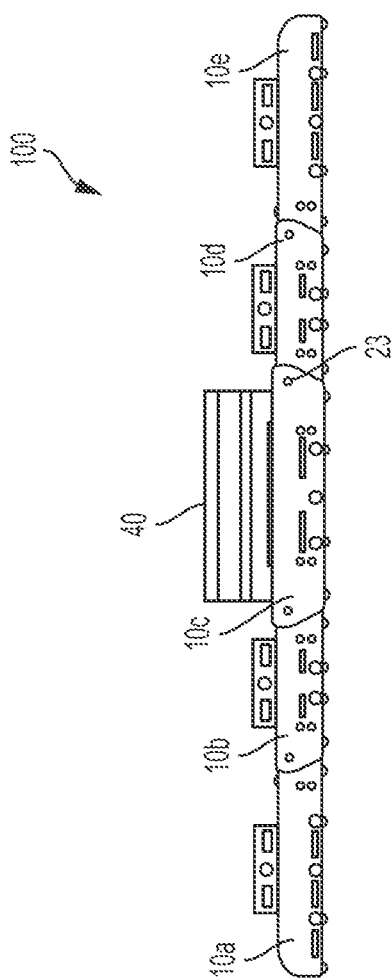
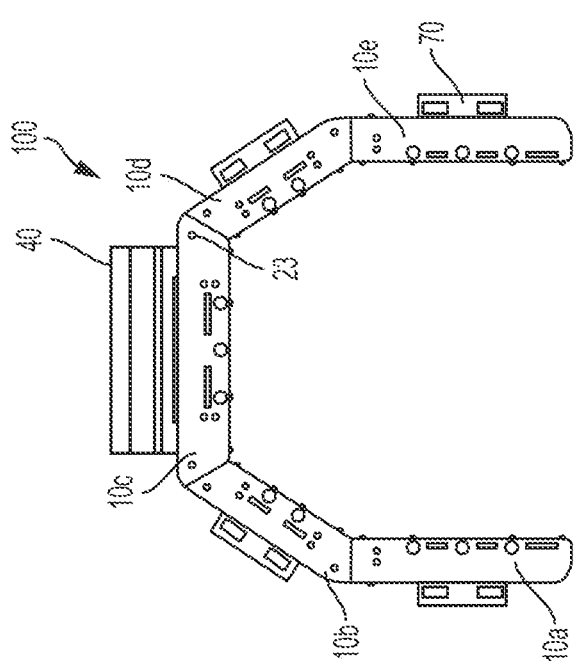
FIG. 1B
FIG. 1A

FIG. 9

Water Loss Baseline

| # | SN# | A | B | C | D | E | Control |
|---|---|---|---|---|---|---|---|
| 1 | SN004 | 3.4 | 3.2 | 4.0 | 5.3 | 4.3 | 4.5 |
| 2 | SN002 | 3.9 | 5.2 | 3.4 | 5.7 | 3.1 | 4.5 |
| 3 | SN001 | 4.7 | 3.6 | 4.1 | 4.1 | 3.9 | 3.1 |
| 4 | SN006 | 6.5 | 6.8 | 7.2 | 6.6 | 5.6 | 7.3 |
| 5 | SN010 | 6.7 | 6.0 | 6.2 | 7.2 | 6.3 | 6.3 |
| 6 | SN012 | 3.9 | 3.6 | 3.9 | 4.6 | 4.1 | 4.3 |
| 7 | SN020 | 7.9 | 8.2 | 6.8 | 6.0 | 9.2 | 7.9 |
| 8 | SN025 | 3.1 | 3.8 | 3.3 | 3.7 | 4.0 | 3.4 |
| 9 | SN013 | 5.0 | 3.4 | 5.2 | 3.9 | 5.2 | 3.8 |
| 10 | SN003 | 4.0 | 3.8 | 3.1 | 3.8 | 3.8 | 5.1 |
| 11 | SN026 | 8.6 | 6.6 | 6.4 | 6.6 | 8.0 | 8.2 |
| 12 | SN015 | 3.5 | 3.1 | 6.3 | 4.9 | 3.5 | 2.9 |
| 13 | SN011 | 2.1 | 3.7 | 1.3 | 2.7 | 2.8 | 2.3 |
| 14 | SN014 | 6.1 | 5.0 | 4.0 | 4.9 | 4.3 | 7.3 |
| 15 | SN007 | 3.7 | 4.0 | 3.3 | 4.6 | 3.6 | 3.4 |
| 16 | SN009 | 4.5 | 4.1 | 3.1 | 3.3 | 3.9 | 4.7 |
| 17 | SN031 | 3.4 | 4.6 | 5.0 | 4.3 | 2.6 | 5.5 |
| 18 | SN008 | 5.6 | 4.4 | 5.9 | 6.9 | 5.6 | 6.3 |
| 19 | SN017 | 8.1 | 6.1 | 6.0 | 9.4 | 6.8 | 7.5 |
| 20 | SN035 | 8.3 | 7.7 | 7.9 | 7.3 | 9.2 | 8.4 |
| 21 | SN018 | 4.4 | 4.7 | 4.7 | 3.2 | 4.7 | 5.4 |
| 22 | SN024 | 4.5 | 6.1 | 5.6 | 2.7 | 4.9 | 3.6 |
| 23 | SN029 | 4.1 | 4.2 | 5.9 | 3.7 | 5.3 | 6.0 |
| 24 | SN019 | 2.2 | 5.7 | 2.4 | 3.6 | 4.9 | 3.3 |
| 25 | SN021 | 5.8 | 6.0 | 4.1 | 5.4 | 6.5 | 5.8 |
| 26 | SN027 | 4.3 | 6.3 | 5.6 | 5.9 | 5.0 | 4.3 |
| 27 | SN028 | 5.5 | 3.8 | 2.9 | 4.3 | 4.0 | 2.4 |
| 28 | SN033 | 2.4 | 3.9 | 1.2 | 3.3 | 1.9 | 1.7 |
| 29 | SN030 | 6.0 | 4.4 | 4.9 | 5.8 | 4.0 | 5.2 |
| 30 | SN023 | 4.6 | 8.8 | 4.3 | 5.9 | 7.2 | 7.1 |
| | Mean | 4.88 | 5.02 | 4.60 | 4.99 | 4.93 | 5.06 |
| | SD | 1.78 | 1.54 | 1.67 | 1.58 | 1.79 | 1.88 |

FIG. 10

Water Loss Post 3 Hours Wear Time

| # | SN# | A | B | C | D | E | Control |
|---|---|---|---|---|---|---|---|
| 1 | SN004 | 2.7 | 0.4 | 0.6 | 2.7 | 0.5 | 3.6 |
| 2 | SN002 | 3.0 | 1.2 | 1.9 | 1.5 | 0.5 | 4.7 |
| 3 | SN001 | 2.8 | 0.1 | 1.2 | 2.7 | 0.3 | 3.3 |
| 4 | SN006 | 2.4 | 1.5 | 0.9 | 4.1 | 0.4 | 5.7 |
| 5 | SN010 | 5.1 | 1.8 | 0.5 | 3.8 | 0.2 | 5.5 |
| 6 | SN012 | 2.9 | 0.8 | 0.8 | 2.7 | 0.2 | 4.0 |
| 7 | SN020 | 4.6 | 0.3 | 1.8 | 4.5 | 0.7 | 6.0 |
| 8 | SN025 | 0.6 | 0.8 | 1.1 | 2.7 | 0.4 | 3.0 |
| 9 | SN013 | 7.0 | 1.8 | 3.3 | 7.5 | 1.2 | 3.6 |
| 10 | SN003 | 1.9 | 0.6 | 0.2 | 1.6 | 0.9 | 2.8 |
| 11 | SN026 | 6.5 | 9.1 | 1.3 | 4.5 | 0.2 | 8.3 |
| 12 | SN015 | 0.9 | 0.6 | 1.7 | 1.0 | 0.5 | 5.4 |
| 13 | SN011 | 1.6 | 0.6 | 0.6 | 1.2 | 2.5 | 0.6 |
| 14 | SN014 | 3.7 | 0.1 | 0.9 | 2.2 | 0.6 | 2.9 |
| 15 | SN007 | 3.5 | 6.0 | 0.9 | 3.7 | 0.0 | 1.7 |
| 16 | SN009 | 2.4 | 0.2 | 0.3 | 4.3 | 0.5 | 4.3 |
| 17 | SN031 | 1.1 | 0.4 | 1.9 | 4.4 | 0.5 | 2.0 |
| 18 | SN008 | 3.5 | 0.6 | 1.5 | 1.0 | 0.5 | 6.1 |
| 19 | SN017 | 4.1 | 0.3 | 0.8 | 6.1 | 3.8 | 4.8 |
| 20 | SN035 | 1.9 | 0.1 | 0.7 | 5.0 | 0.1 | 3.9 |
| 21 | SN018 | 3.5 | 0.6 | -0.8 | 1.8 | 0.3 | 5.4 |
| 22 | SN024 | 2.6 | 0.0 | 1.5 | 3.7 | 0.2 | 2.0 |
| 23 | SN029 | 3.3 | -0.1 | 0.3 | 2.5 | 1.1 | 5.2 |
| 24 | SN019 | 2.8 | 0.2 | 0.1 | 2.3 | 1.1 | 5.6 |
| 25 | SN021 | 3.8 | 1.0 | 0.9 | 3.3 | 0.1 | 6.2 |
| 26 | SN027 | 0.9 | 0.7 | 1.0 | 3.4 | 0.9 | 4.0 |
| 27 | SN028 | 4.3 | 0.2 | 1.3 | 3.6 | 0.5 | 3.2 |
| 28 | SN033 | 0.9 | 1.9 | 0.4 | 1.1 | 0.7 | 3.1 |
| 29 | SN030 | 4.3 | 0.8 | 0.8 | 4.7 | 0.0 | 3.1 |
| 30 | SN023 | 5.5 | 0.8 | 0.3 | 1.9 | 0.7 | 6.8 |
| | Mean | 3.14 | 1.11 | 0.96 | 3.18 | 0.67 | 4.22 |
| | SD | 1.61 | 1.88 | 0.73 | 1.57 | 0.76 | 1.69 |

FIG. 11

Degree of Occlusion at Post 3 Hours Wear Time

| # | SN# | A | B | C | D | E | Control |
|---|---|---|---|---|---|---|---|
| 1 | SN004 | 21.4 | 89.1 | 84.4 | 48.3 | 88.0 | 21.3 |
| 2 | SN002 | 21.7 | 77.4 | 43.1 | 73.9 | 84.1 | -4.9 |
| 3 | SN001 | 39.0 | 97.4 | 71.1 | 35.6 | 93.3 | -6.7 |
| 4 | SN006 | 63.0 | 78.1 | 87.4 | 37.0 | 93.0 | 22.6 |
| 5 | SN010 | 24.7 | 69.6 | 91.3 | 46.8 | 96.8 | 12.8 |
| 6 | SN012 | 24.7 | 78.5 | 80.5 | 40.1 | 94.4 | 5.5 |
| 7 | SN020 | 41.9 | 96.9 | 73.6 | 24.5 | 92.7 | 24.4 |
| 8 | SN025 | 79.8 | 79.7 | 68.2 | 27.2 | 89.5 | 12.1 |
| 9 | SN013 | -40.4 | 47.7 | 37.0 | -92.5 | 76.8 | 6.1 |
| 10 | SN003 | 52.2 | 84.7 | 93.6 | 58.6 | 77.6 | 44.7 |
| 11 | SN026 | 24.1 | -37.8 | 79.8 | 32.3 | 97.9 | -0.4 |
| 12 | SN015 | 74.0 | 81.2 | 72.6 | 80.2 | 84.8 | -82.6 |
| 13 | SN011 | 22.5 | 85.2 | 51.5 | 56.0 | 12.3 | 73.5 |
| 14 | SN014 | 39.3 | 98.3 | 77.8 | 55.7 | 85.0 | 60.0 |
| 15 | SN007 | 3.7 | -51.5 | 73.1 | 20.0 | 98.8 | 49.9 |
| 16 | SN009 | 46.0 | 94.5 | 90.0 | -32.0 | 86.8 | 8.3 |
| 17 | SN031 | 66.8 | 91.9 | 62.5 | -1.2 | 80.2 | 63.8 |
| 18 | SN008 | 37.7 | 85.7 | 74.0 | 85.3 | 91.8 | 2.9 |
| 19 | SN017 | 49.3 | 94.8 | 86.1 | 35.0 | 45.0 | 36.1 |
| 20 | SN035 | 76.9 | 98.2 | 90.6 | 31.4 | 98.8 | 53.6 |
| 21 | SN018 | 19.7 | 88.2 | 115.9 | 43.9 | 93.6 | -1.0 |
| 22 | SN024 | 42.8 | 100.2 | 73.9 | -34.4 | 96.5 | 44.9 |
| 23 | SN029 | 18.7 | 101.6 | 94.4 | 32.6 | 80.1 | 13.7 |
| 24 | SN019 | -31.4 | 96.4 | 94.3 | 37.7 | 77.4 | -68.8 |
| 25 | SN021 | 34.5 | 83.2 | 77.5 | 39.3 | 97.9 | -7.9 |
| 26 | SN027 | 78.8 | 88.2 | 82.7 | 41.7 | 82.0 | 7.5 |
| 27 | SN028 | 22.4 | 93.9 | 57.0 | 15.7 | 88.3 | -34.6 |
| 28 | SN033 | 60.8 | 52.2 | 64.4 | 67.6 | 61.9 | -76.7 |
| 29 | SN030 | 29.6 | 80.7 | 83.5 | 18.6 | 99.3 | 40.1 |
| 30 | SN023 | -20.9 | 91.1 | 92.9 | 68.3 | 90.8 | 5.4 |
| | Mean | 34.10 | 77.18 | 77.50 | 33.11 | 84.51 | 10.85 |
| | SD | 30.03 | 35.45 | 16.48 | 36.20 | 17.92 | 38.45 |

FIG. 12

Water Loss Baseline

| # | SN# | Code E | Code W | Code X | Code Y | Code Z | Control |
|---|---|---|---|---|---|---|---|
| 1 | SN007 | 3.6 | 5.6 | 6.3 | 5.8 | 6.0 | 5.6 |
| 2 | SN012 | 5.0 | 4.3 | 3.3 | 4.0 | 4.2 | 3.4 |
| 3 | SN001 | 3.5 | 1.4 | 2.1 | 1.3 | 2.5 | 1.1 |
| 4 | SN002 | 2.0 | 1.9 | 2.1 | 1.3 | 2.2 | 4.0 |
| 5 | SN008 | 6.1 | 5.8 | 4.1 | 4.4 | 5.8 | 6.3 |
| 6 | SN011 | 5.8 | 3.6 | 3.4 | 2.6 | 4.3 | 3.6 |
| 7 | SN006 | 2.5 | 2.6 | 2.1 | 3.2 | 1.2 | 2.0 |
| 8 | SN003 | 3.1 | 4.9 | 2.8 | 3.8 | 2.9 | 2.4 |
| 9 | SN005 | 4.7 | 8.0 | 5.8 | 6.2 | 6.4 | 6.2 |
| 10 | SN010 | 4.1 | 4.6 | 4.7 | 3.8 | 3.6 | 4.2 |
| 11 | SN016 | 1.9 | 2.1 | 1.2 | 3.4 | 1.7 | 3.0 |
| 12 | SN038 | 2.6 | 2.7 | 2.8 | 3.4 | 3.5 | 3.0 |
| 13 | SN013 | 3.5 | 4.7 | 6.7 | 5.1 | 4.1 | 4.6 |
| 14 | SN031 | 2.3 | 1.7 | 1.2 | 2.4 | 2.3 | 2.3 |
| 15 | SN024 | 3.5 | 3.5 | 3.3 | 3.8 | 2.6 | 4.0 |
| 16 | SN023 | 7.5 | 7.6 | 9.0 | 5.8 | 7.6 | 7.8 |
| 17 | SN025 | 5.3 | 5.0 | 5.1 | 3.8 | 6.1 | 6.5 |
| 18 | SN014 | 4.0 | 2.0 | 2.7 | 5.4 | 3.3 | 3.9 |
| 19 | SN026 | 2.4 | 2.4 | 2.7 | 2.3 | 3.4 | 3.1 |
| 20 | SN015 | 2.1 | 1.9 | 2.8 | 1.7 | 2.3 | 2.1 |
| 21 | SN037 | 5.3 | 4.8 | 4.2 | 5.8 | 5.1 | 5.4 |
| 22 | SN021 | 4.2 | 3.7 | 4.6 | 3.1 | 4.3 | 4.3 |
| 23 | SN022 | 4.0 | 3.0 | 5.2 | 2.3 | 3.3 | 4.0 |
| 24 | SN033 | 5.8 | 5.5 | 4.6 | 4.0 | 4.4 | 5.5 |
| 25 | SN018 | 4.1 | 4.2 | 4.6 | 3.6 | 5.2 | 4.4 |
| 26 | SN020 | 3.8 | 5.1 | 4.2 | 4.0 | 4.4 | 3.9 |
| 27 | SN034 | 3.3 | 3.6 | 4.1 | 3.6 | 4.9 | 4.3 |
| 28 | SN028 | 5.1 | 3.6 | 6.5 | 5.3 | 5.1 | 4.7 |
| 29 | SN027 | 4.7 | 6.1 | 5.6 | 3.3 | 3.9 | 3.4 |
| 30 | SN029 | 5.3 | 5.4 | 3.5 | 4.1 | 4.9 | 4.7 |
| | Mean | 4.04 | 4.04 | 4.04 | 3.76 | 4.04 | 4.11 |
| | SD | 1.38 | 1.71 | 1.76 | 1.33 | 1.50 | 1.49 |

FIG. 13

Water Loss
Post 3 Hours Wear Time

| # | SN# | Code E | Code W | Code X | Code Y | Code Z | Control |
|---|---|---|---|---|---|---|---|
| 1 | SN007 | 0.3 | 0.2 | 2.6 | 0.7 | 2.2 | 4.4 |
| 2 | SN012 | 0.5 | -0.1 | 1.1 | 0.1 | 0.7 | 4.1 |
| 3 | SN001 | -0.2 | 1.1 | 2.2 | 1.2 | 2.3 | 1.1 |
| 4 | SN002 | 0.3 | 1.2 | 1.3 | 0.8 | 0.5 | 4.6 |
| 5 | SN008 | 0.7 | 0.5 | 1.0 | 0.1 | 3.6 | 5.1 |
| 6 | SN011 | 1.1 | 1.1 | 1.2 | 0.7 | 1.2 | 4.1 |
| 7 | SN006 | 0.6 | 0.5 | 1.6 | 1.2 | 1.4 | 2.0 |
| 8 | SN003 | 1.1 | 0.6 | 1.4 | 1.0 | 4.1 | 3.9 |
| 9 | SN005 | 0.4 | -0.6 | 2.0 | -0.2 | 2.3 | 3.4 |
| 10 | SN010 | 0.1 | 0.4 | 2.5 | 0.3 | 2.8 | 4.0 |
| 11 | SN016 | -0.2 | -0.3 | 1.0 | -0.3 | 1.1 | 2.1 |
| 12 | SN038 | 2.5 | 0.5 | 2.2 | -0.1 | 2.6 | 4.5 |
| 13 | SN013 | 0.2 | -0.1 | 3.7 | -0.1 | 3.1 | 4.8 |
| 14 | SN031 | 0.1 | 0.2 | 1.2 | 0.2 | 1.8 | 2.4 |
| 15 | SN024 | -0.6 | 0.6 | 2.9 | -0.2 | 2.4 | 4.0 |
| 16 | SN023 | 0.0 | -0.2 | 5.2 | 0.2 | 3.8 | 7.9 |
| 17 | SN025 | -0.4 | 0.4 | 5.2 | 0.1 | 4.7 | 9.2 |
| 18 | SN014 | 0.4 | 0.6 | 1.7 | 0.2 | 2.6 | 4.1 |
| 19 | SN026 | -0.7 | 0.3 | 1.4 | 0.6 | 2.0 | 2.5 |
| 20 | SN015 | -0.2 | -0.3 | 1.4 | -0.1 | 1.7 | 3.1 |
| 21 | SN037 | 0.8 | -0.4 | 3.0 | 0.1 | 2.6 | 7.1 |
| 22 | SN021 | 0.7 | 1.0 | 3.0 | 0.8 | 1.9 | 5.1 |
| 23 | SN022 | 0.9 | 0.8 | 1.8 | 0.7 | 2.5 | 3.8 |
| 24 | SN033 | 0.0 | 0.8 | 3.8 | 0.2 | 4.3 | 5.4 |
| 25 | SN018 | 1.0 | 0.9 | 1.1 | 0.5 | 2.9 | 4.6 |
| 26 | SN020 | 1.2 | 1.2 | 3.5 | 0.6 | 1.2 | 3.9 |
| 27 | SN034 | 0.2 | 0.4 | 3.6 | -0.1 | 2.6 | 4.7 |
| 28 | SN028 | 0.0 | 0.3 | 3.0 | 1.1 | 4.5 | 5.6 |
| 29 | SN027 | 0.4 | 0.4 | 4.7 | 1.0 | 1.6 | 4.9 |
| 30 | SN029 | 0.3 | 0.4 | 2.9 | 0.1 | 2.0 | 4.6 |
| | Mean | 0.39 | 0.41 | 2.43 | 0.37 | 2.42 | 4.36 |
| | SD | 0.63 | 0.49 | 1.25 | 0.45 | 1.09 | 1.67 |

FIG. 14

Degree of Occlusion at Post 3 Hours Wear Time

| # | SN# | Code E | Code W | Code X | Code Y | Code Z | Control |
|---|---|---|---|---|---|---|---|
| 1 | SN007 | 91.3 | 96.2 | 59.2 | 88.7 | 62.5 | 22.0 |
| 2 | SN012 | 90.3 | 102.7 | 66.4 | 97.6 | 82.7 | -21.3 |
| 3 | SN001 | 104.5 | 20.3 | -7.5 | 12.4 | 8.9 | 2.8 |
| 4 | SN002 | 85.7 | 35.9 | 38.9 | 40.3 | 79.7 | -14.4 |
| 5 | SN008 | 89.0 | 91.3 | 74.3 | 97.9 | 37.3 | 18.8 |
| 6 | SN011 | 81.4 | 69.1 | 64.7 | 73.0 | 72.6 | -13.0 |
| 7 | SN006 | 77.8 | 81.6 | 23.2 | 63.3 | -18.5 | 2.2 |
| 8 | SN003 | 65.3 | 87.1 | 50.9 | 74.3 | -41.4 | -63.6 |
| 9 | SN005 | 91.5 | 107.7 | 64.8 | 102.9 | 64.8 | 45.1 |
| 10 | SN010 | 97.7 | 91.2 | 46.3 | 92.6 | 22.3 | 4.7 |
| 11 | SN016 | 110.8 | 115.3 | 22.8 | 110.0 | 33.6 | 31.0 |
| 12 | SN038 | 4.8 | 82.8 | 22.5 | 103.9 | 26.3 | -52.9 |
| 13 | SN013 | 94.7 | 101.2 | 45.0 | 102.8 | 24.5 | -4.5 |
| 14 | SN031 | 94.9 | 88.8 | 0.9 | 92.1 | 18.4 | -3.3 |
| 15 | SN024 | 116.7 | 82.7 | 13.1 | 104.1 | 10.3 | -0.6 |
| 16 | SN023 | 99.5 | 103.1 | 42.2 | 96.3 | 49.5 | -1.9 |
| 17 | SN025 | 106.9 | 91.9 | -3.0 | 97.1 | 22.9 | -42.4 |
| 18 | SN014 | 91.0 | 71.2 | 38.0 | 97.0 | 20.0 | -6.7 |
| 19 | SN026 | 128.0 | 89.4 | 46.4 | 72.9 | 41.2 | 18.1 |
| 20 | SN015 | 107.5 | 115.3 | 51.9 | 106.8 | 28.4 | -50.5 |
| 21 | SN037 | 84.3 | 108.3 | 29.8 | 99.0 | 49.9 | -32.8 |
| 22 | SN021 | 83.2 | 73.3 | 33.9 | 76.1 | 55.9 | -19.3 |
| 23 | SN022 | 77.2 | 73.1 | 66.3 | 67.8 | 25.5 | 3.8 |
| 24 | SN033 | 99.5 | 85.5 | 18.1 | 94.0 | 3.0 | 2.0 |
| 25 | SN018 | 75.2 | 78.7 | 76.5 | 86.5 | 45.3 | -3.5 |
| 26 | SN020 | 67.6 | 77.3 | 17.6 | 85.5 | 72.7 | -0.3 |
| 27 | SN034 | 92.6 | 87.7 | 12.3 | 101.9 | 46.9 | -8.9 |
| 28 | SN028 | 99.8 | 90.5 | 54.4 | 79.1 | 11.5 | -19.7 |
| 29 | SN027 | 92.3 | 94.1 | 15.5 | 70.8 | 58.4 | -43.9 |
| 30 | SN029 | 95.1 | 93.4 | 18.7 | 96.5 | 58.4 | 1.2 |
| | Mean | 89.87 | 86.22 | 36.80 | 86.11 | 35.78 | -8.39 |
| | SD | 21.07 | 20.06 | 23.45 | 20.97 | 28.59 | 24.95 |

METHODS FOR PHOTODYNAMIC THERAPY

CROSS REFERENCE TO RELATED APPLICATION

This application is a continuation of U.S. application Ser. No. 17/876,224, filed Jul. 28, 2022, which is a divisional of U.S. application Ser. No. 17/487,698, filed Sep. 28, 2021, now U.S. Pat. No. 11,571,478, which is a continuation of U.S. application Ser. No. 17/109,311, filed Dec. 2, 2020, now U.S. Pat. No. 11,135,293, which is a continuation of U.S. application Ser. No. 16/438,702, filed Jun. 12, 2019, now U.S. Pat. No. 11,077,192, which is a continuation of U.S. application Ser. No. 15/869,164, filed Jan. 12, 2018, now U.S. Pat. No. 10,357,567, the entire contents of all of which is incorporated herein by reference.

FIELD

The present disclosure relates generally to methods for photodynamic therapy.

BACKGROUND

Photodynamic therapy (PDT), photodynamic diagnosis (PD), or photochemotherapy is generally used to treat and/or diagnose several types of ailments in or near the skin or other tissues, such as those in a body cavity. For example, photodynamic therapy or photodynamic diagnosis may be used for treatment or diagnosis of actinic keratosis of the upper extremities (e.g., the dorsal surface of the hand or forearms), scalp or facial areas of a patient. In addition, such techniques may be used for treatment and diagnosis of other indications (e.g., acne, warts, psoriasis, photo-damaged skin, cancer) and other areas of the patient (e.g., the legs or portions of the arms other than the forearms).

During one form of photodynamic therapy, a patient is first administered a photoactivatable agent or a precursor of a photoactivatable agent that accumulates in the tissue to be treated. The area in which the photoactivatable agent is administered is then exposed to visible light, which causes chemical and/or biological changes in the agent. These changes allow the agent to then selectively locate, destroy, or alter the target tissue while, at the same time, causing at most only mild and reversible damage to other tissues in the treatment area. One example of a precursor of a photoactivatable agent is 5-aminolevulinic acid ("ALA"), which is commonly used in photodynamic therapy of actinic keratosis. As they are used here, the terms ALA or 5-aminolevulinic acid refer to ALA itself, precursors thereof, esters thereof and pharmaceutically acceptable salts of the same. Photosensitization following application of a topical composition (e.g., a topical solution or emulsion) containing ALA occurs through the metabolic conversion of aminolevulinic acid to protoporphyrin IX (PpIX), as discussed in more detail below. PpIX is a photosensitizer which accumulates in the skin.

For photodynamic therapy to be effective, it is desirable to have a power output that can be controlled for intensity and duration, among other factors. Illuminators are typically used to provide the proper uniformity of light for treatment purposes. These devices generally include a light source (e.g., a fluorescent tube or LED), coupling elements that direct, filter or otherwise conduct emitted light so that it arrives at its intended target in a usable form, and a control system that starts and stops the production of light when necessary.

Photodynamic therapy may be carried out using certain compositions, such as ALA, in connection with illuminators as described above. Such compositions and/or devices are disclosed, for example, in (1) U.S. Pat. No. 5,954,703 to Golub, entitled "Method and apparatus for applying 5-aminolevulinic acid," issued on Sep. 21, 1999, (2) U.S. Pat. No. 6,223,071 to Lundahl et al., entitled "Illuminator for photodynamic therapy and diagnosis which produces substantially uniform intensity visible light," issued on Apr. 24, 2001, (3) U.S. patent application Ser. No. 15/371,363 to Boyajian et al., entitled "Method And Apparatus For Applying A Topical Solution," published on Jun. 8, 2017 as U.S. Pub. No. 2017/0157379, (4) International Application No. PCT/US2016/056572 to Boyajian et al., entitled "Adjustable Illuminator For Photodynamic Therapy And Diagnosis," published on Apr. 20, 2017 as WO 2017/066270, (5) U.S. patent application Ser. No. 15/292,731 to Boyajian et al., entitled "Adjustable Illuminator For Photodynamic Therapy And Diagnosis," published on Apr. 20, 2017 as U.S. Pub. No. 2017/0106205, and (6) U.S. patent application Ser. No. 15/487,991 to Boyajian et al., entitled "Adjustable Illuminators And Methods For Photodynamic Therapy And Diagnosis," published on Aug. 3, 2017 as U.S. Pub. No. 2017/0216616. The entire contents of the foregoing patents and/or patent applications (1)-(6) are incorporated herein by reference for background information and the compositions, devices, processes and techniques relating to photodynamic therapy and diagnosis disclosed therein.

SUMMARY

Through research and experimentation in photodynamic therapeutic techniques, the inventors have found that covering a treatment area with polyethylene (such as low density polyethylene (LDPE)) for a period of time prior to light treatment is particularly effective to minimize transepidermal water loss from the treatment area. Surprisingly, it was found that a polymeric barrier having a degree of occlusion more than 65% (such as LDPE) was superior to other materials such as polyurethane and polyvinylidene chloride (PVdC). The low density polyethylene can be applied to a wide variety of treatment areas, such as the arms, legs, chest, back, portions of the head, and the like, and can be used with drugs other than ALA.

According to one aspect of the disclosure, a method of enhancing penetration of a topical composition of 5-aminolevulinic acid (ALA) into tissue for photodynamic therapy is disclosed. The method includes topically applying ALA to a treatment area to be treated with photodynamic therapy. The method further includes, after the ALA is applied to the treatment area, covering the treatment area with a polymeric barrier have a degree of occlusion of 65% or more.

According to another aspect of the disclosure, a method of enhancing penetration of a topical composition of 5-aminolevulinic acid (ALA) into tissue for photodynamic therapy is disclosed. The method includes topically applying ALA to a treatment area to be treated with photodynamic therapy. The method further includes, after the ALA is applied to the treatment area, covering the treatment area with a low density polyethylene barrier. The treatment area is covered with the low density polyethylene barrier prior to light treatment to minimize transepidermal water loss from the treatment area.

According to still another aspect of the disclosure, a method of photodynamic treatment of the stratum corneum is disclosed. The method includes applying 5-aminolevulinic acid (ALA) to a lesion on the stratum corneum and reducing evaporation from a portion of the stratum corneum including an area where the lesion is present. The method further includes heating the area where the lesion is present before or during illumination of the area where the lesion is present.

According to a further aspect of the disclosure, a method of using 5-aminolevulinic acid (ALA) and a low density polyethylene barrier is disclosed. The method includes contacting a treatment site with a composition comprising the ALA so as to wet the treatment site, and, following wetting of the treatment site, covering the wetted treatment site with the low density polyethylene barrier.

According to an additional aspect of the disclosure, a method of enhancing penetration of a topical composition of 5-aminolevulinic acid (ALA) HCl into tissue for photodynamic therapy is disclosed. The method includes topically applying the composition to a treatment area to be treated with photodynamic therapy. The method further includes, after the composition is applied to the treatment area, covering the treatment area with a low density polyethylene barrier prior to light treatment to minimize transepidermal water loss from the treatment area. The composition exhibits a mean plasma concentration ($C_{max}$) value of ALA less than about 110 ng/mL when the ALA HCl is applied in an amount of 354 mg.

BRIEF DESCRIPTION OF THE DRAWINGS

The details of one or more embodiments are set forth in the accompanying drawings and the description below. Other features, aspects, and advantages will become apparent from the description, the drawings, and the claims. In the drawings, like reference numerals are used throughout the various views to designate like components. The drawings are briefly described below.

FIGS. 1A-1B show top views of a main body of an illuminator according to an exemplary embodiment.

FIG. 9 is a table containing baseline water loss data for the materials referred to in FIGS. 5-6.

FIG. 10 is a table containing water loss data following three hours of wear time for the materials referred to in FIGS. 5-6.

FIG. 11 is a table containing occlusion data for the materials referred to in FIGS. 5-6.

FIG. 12 is a table containing baseline water loss data for the materials referred to in FIGS. 7-8.

FIG. 13 is a table containing water loss data following three hours of wear time for the materials referred to in FIGS. 7-8.

FIG. 14 is a table containing occlusion data for the materials referred to in FIGS. 7-8.

Figure 2B:
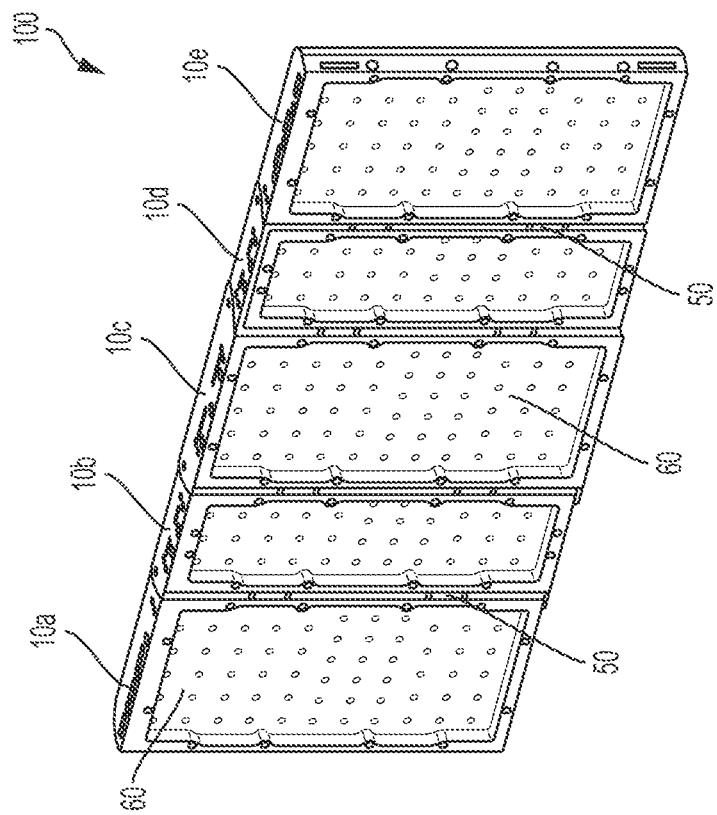
FIGS. 2A-2B show perspective views of the main body of the illuminator of FIGS. 1A-1B.

It will be recognized that some or all of the figures are schematic representations for purposes of illustration. The figures are provided for the purpose of illustrating one or more embodiments with the explicit understanding that they will not be used to limit the scope or the meaning of the claims.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). The following terms are used throughout and are as defined below.

As used herein and in the appended claims, singular articles such as "a" and "an" and "the" and similar references in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illustrate the embodiments and does not pose a limitation on the scope of the claims unless otherwise stated. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The expression "comprising" means "including, but not limited to." Thus, other non-mentioned substances, additives, devices or steps may be present. Unless otherwise specified, "a" or "an" means one or more.

Unless otherwise indicated, all numbers expressing quantities of properties, parameters, conditions, and so forth, used in the specification and claims are to be understood as being modified in all instances by the term "about." Accordingly, unless indicated to the contrary, the numerical parameters set forth in the following specification and attached claims are approximations. Any numerical parameter should at least be construed in light of the number reported significant digits and by applying ordinary rounding techniques. The term "about" when used before a numerical designation, e.g., temperature, time, amount, and concentration including range, indicates approximations which may vary by (+) or (−) 10%, 5% or 1%.

As will be understood by one of skill in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

Exemplary Illuminator

Figure 2A:
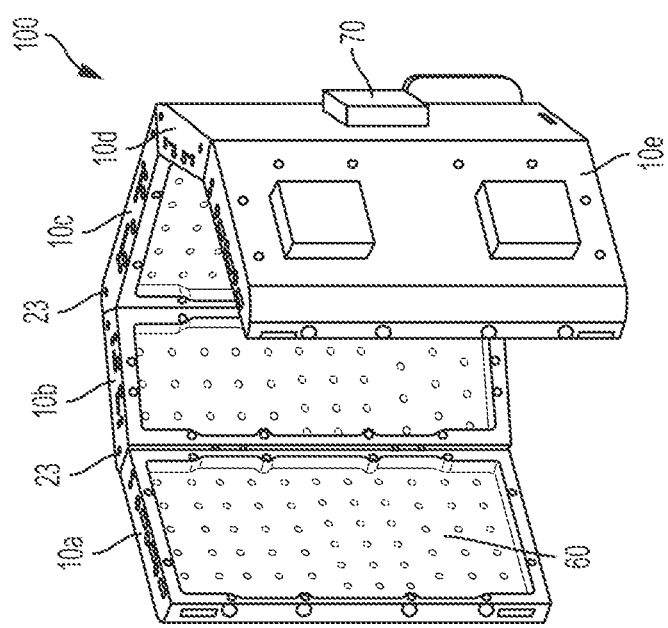

FIGS. 1A-1B and 2A-2B illustrate one embodiment of a configurable illuminator as may be used in accordance with the present disclosure. The illuminator includes a main body 100, which preferably has a plurality of individual panels (e.g., panels 10a-10e, each of which are connected in a rotatable manner via nested hinges 50). As shown in FIGS. 2A-2B, on at least one side of a panel, a tab 23 may extend out from both the top and bottom of the panel. The tabs 23 are configured such that a side of an adjacent panel may be received between the tabs 23, as shown in FIG. 2A, and the hinges 50 are between the tabs 23. Each panel contains an array of light emitting diodes (LED) 60. The number of individual LEDs arranged in a given array is not particularly limited. Alternatively, other types of light sources may be used, such as fluorescent or halogen lamps. The LED arrays 60 emit light at an appropriate wavelength according to the intended treatment or to activate the particular photoactivatable agent used in treatment or diagnosis.

In at least one embodiment, when ALA is used as a precursor of a photoactivatable agent for the treatment of actinic keratosis, the LED arrays 60 preferably emit blue light having wavelengths at or above 400 nanometers (nm), for example, about 430 nm, about 420 nm or, for example, 417 nm. However, the LED arrays 60 may also emit visible light in other ranges of the spectrum, such as in the green and/or red ranges between 400 and 700 nm, for example, about 625 nm to 640 nm or, for example, 635 nm. For example, the LED arrays 60 may also emit light having wavelengths of 510 nm, 540 nm, 575 nm, 630 nm, or 635 nm. In addition, the LED arrays 60 may be configured to emit light continuously or the LED arrays 60 may be configured to flash the diodes on and off based on a predetermined interval. Furthermore, the LED arrays 60 may be configured such that only one wavelength of light (e.g., blue) is emitted. Alternatively, the LED arrays 60 may be configured such that two or more wavelengths of light are emitted from the arrays. For example, the LED arrays 60 may be configured to alternately emit blue light and red light for treatment purposes. In one embodiment, the LED arrays may also emit red light having wavelengths of 570 to 670 nm.

In one embodiment of the present disclosure, blue light having a wavelength of approximately 417 nm is applied at an intensity of 10 mW/cm$^2$ for 1000 seconds to provide a dose of 10 J/cm$^2$. However, the intensity may be increased (for example, doubled) to reduce the treatment time. For example, the intensity may be increased so as to reduce the treatment time by about one-half. In other embodiments, red light (such as red light generated by light emitting diodes (LEDs) at, for example, 635 nm) may be used. The red light can provide a dose of, for example, 10 to 75 J/cm$^2$ (such as 37 J/cm$^2$), e.g., within 10 minutes.

The ALA can be applied using an applicator as described below, using, for example, a 20% solution of ALA, or can be applied by other means such as glove protected fingers or a spatula. The ALA can be applied in, for example, liquid or gel form and can be applied beyond the lesions to be treated. In certain applications, materials other than low density polyethylene may be used as long as they have a degree of occlusion of 65% or more. In certain applications, certain materials may be used as long as they have a degree of occlusion of 75% or more.

Figure 3:
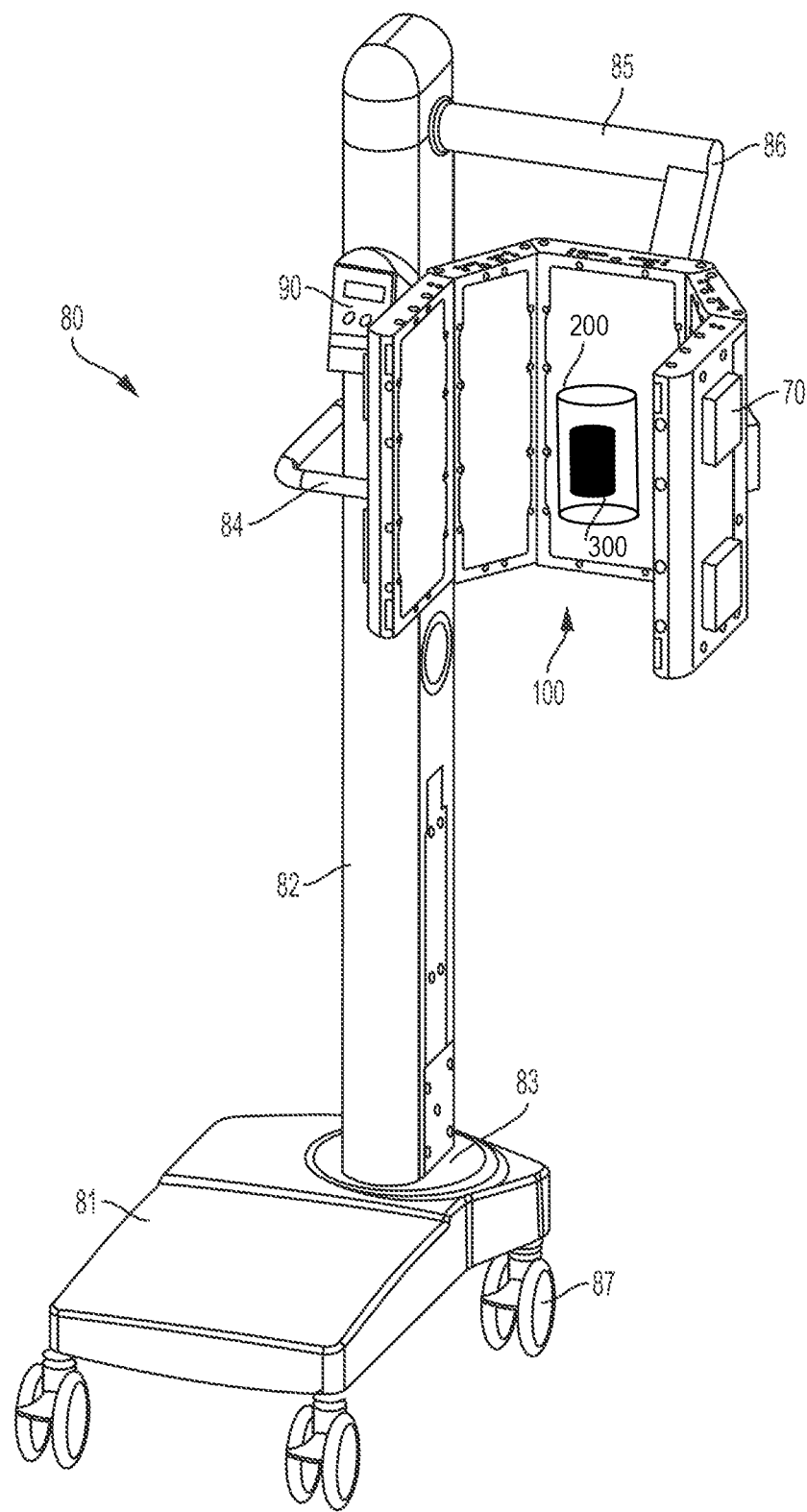
FIG. 3 shows a perspective view of the illuminator having the main body of FIGS. 1A-1B mounted to a stand.

Referring again to the exemplary illuminator shown in FIGS. 1A-1B, the main body 100 of the illuminator may include a mounting head 40. The mounting head 40 may allow for the main body 100 to be mounted to a movable stand 80, which is shown in FIG. 3, to allow a user to easily move the main body 100 to the appropriate treatment position. The stand 80 includes a base 81 and a vertical pillar 82. The base 81 may further include wheels 87 at its bottom in order to allow the user to horizontally move the illuminator to an appropriate position. The wheels 87 may include locks, such that the stand 80 is prevented from further horizontal movement once positioned. In addition, the vertical pillar 82 may be attached to the base 81 at a pivot point 83.

At a top end, the vertical pillar 82 includes a connecting arm 85, which may serve as a mounting structure for the main body 100. The connecting arm 85 includes a hinge point 86 such that the main body 100 can be moved vertically relative to the stand 80. The stand 80 may also include a stabilization arm 84. Once the stand 80 and main body 100 is positioned, the stabilization arm 84 may be attached to the main body 100 to prevent unwanted movement of the main body 100 during treatment. As further shown in FIG. 3, a controller and power supply 90 is mounted to the stand 80 in order to supply electrical power to the main body 100 and allow the user to control the main body 100 for treatment purposes. Alternatively, the controller and power supply 90 may be directly mounted to the main body 100. In order to provide a cooling system for the LED arrays 60, one or more fans 70 may be mounted onto each of the panels, as shown in FIG. 3.

The controller and power supply 90 may be also connected to the panels to regulate power to the light source to achieve a desired uniformity and intensity for the target treatment. The control unit may be implemented as hardware, software, or a combination of both, such as a memory device storing a computer program and a processor to execute the program. Alternatively, each panel may have a dedicated control unit to regulate power to the individual LED array on a given panel to allow for fine-tuning of the illuminator, which may further enhance uniformity and increase efficiency. The LED arrays 60 may be individually configured to increase the intensity of light emitted from certain diodes to achieve particular illumination effects.

The illuminator may further include a timer included in the controller and power supply 90, which can indicate to the user the appropriate length of exposure time for the particular treatment. The illuminator may also be programmed with pre-stored light dosing parameters to allow the user to select a desired treatment type. The pre-stored parameters may include, for example, pre-stored settings for exposure time, light intensity, and outputted wavelength. Based on the selected treatment, the illuminator is automatically configured to provide the correct lighting dosage by being supplied with the appropriate power output to achieve the required uniformity for the treatment.

Alternatively, the illuminator can be provided with sensors that detect the size of the treatment area positioned in front of the illuminator. The sensors then determine the correct light dosing parameters based on the sensed treatment area. The sensors may detect the adjusted position of the illuminator manually set by the user. The detected position of the illuminator may then be used to indicate the intended treatment area. Appropriate light dosing parameters for the specific treatment area may then be provided based on the detected position set by the user.

Adjustable illuminators as described above allow for an infinite amount of configurations that can be adapted for the targeted treatment area. The configurations may range from a flat-plane emitter (as shown in FIGS. 1B and 2B) to a substantially U-shaped configuration (as shown in FIGS. 1A and 2A). Not only can the adjustable illuminator effectively deliver a uniform light intensity to surfaces such as the face or scalp, but the adjustable illuminator can also provide a device that can easily be configured to treat other portions of a patient's body, in particular, those having smaller curved surfaces, such as the arms and legs, and in particular, the upper extremities Moreover, the adjustable illuminator may also be easily positioned to deliver a uniform light intensity to larger treatment areas, such as the back or chest.

The illuminator may irradiate the lesions with a uniform intensity red light for a prescribed period. In certain embodiments, the illuminator irradiates the lesions with a uniform intensity blue light for a first prescribed period and then irradiates the lesions with a uniform intensity red light for a second prescribed period. For example, in some embodiments, the illuminator is configured to irradiate the lesions with a uniform intensity blue light (e.g., 417 nm) at a low intensity (e.g., about 0.1 J/cm$^2$ to about 2 J/cm$^2$) to photobleach, for example, protoporphyrin IX (PpIX) present at the surface of the patient's skin, and irradiate the lesions with a uniform intensity red light (e.g., 635 nm) at a high intensity (e.g., about 30 J/cm$^2$ to about 150 J/cm$^2$) to activate PpIX present at deeper layers of the patient's skin, thus avoiding potential damage to the upper layers of the patient's skin.

Furthermore, since the total light dose (J/cm$^2$) is equal to irradiance (mW/cm$^2$) multiplied by time (sec), an additional parameter to be controlled for delivery of the correct treatment light dose is exposure time. This may be accomplished by the timer described above, which can control the electrical power supplied to the LED arrays 60 appropriately, and which can be set by the physician. Data has shown that 10 J/cm$^2$ delivered from a source with an irradiance density of 10 mW/cm$^2$, or an irradiance density of about 9.3 to about 10.7 mW/cm$^2$, produces clinically acceptable results for desired treatment areas (e.g., face, scalp, extremities). An adjustable illuminator may deliver an irradiance density of 20 mW/cm$^2$ for an exposure time of 500 seconds (8 min. 20 sec) to deliver a clinically acceptable light dose of 10 J/cm$^2$. In certain embodiments, a lower intensity may be used with a longer exposure time (e.g., 1,000 seconds of exposure time for a light dose of 10 J/cm$^2$). Alternatively, the adjustable illuminator may include higher power ranges, such as 30 mW/cm$^2$, over an exposure time resulting in a light dose of 10 J/cm$^2$. A selected light dose may also be administered by additionally or alternatively varying the irradiance density over treatment time.

In at least one embodiment, a heating element (a heat source) may be provided. The heat source may be used to heat the region to be treated. According to one embodiment, a method of treatment includes warming up an illuminator so as to cause heat to be emitted from the illuminator, and exposing a treatment site to the illuminator. The heat accelerates the conversion of the ALA to porphyrin (e.g., photosensitive porphyrin or proto porphyrin). The relationship between temperature exposure and ALA conversion is non-linear, and the enzymatic pathways responsible for the conversion are highly sensitive to temperature. In at least one embodiment, increasing the temperature by approximately 2° C. may approximately double the rate of production of protoporphyrin IX (PpIX), for example.

The heat may be applied before or during illumination with the illuminator. For example, first, the ALA may be applied. Next, the heating element may be activated, to apply heat to the patient's skin for a first treatment period for a thermal soak, which may be 20-30 minutes, for example. During the heating, the treatment site may or may not be occluded. In other words, the treatment site may be heated while being occluded.

Following the first treatment period, light may be applied for a second treatment period, e.g., about 8-15 minutes. In at least one embodiment, the heat source may be an infrared quartz heater. In at least one embodiment, the heat source may comprise frame mounted resistance tape heaters or a plurality of heaters, including at least one selected from the group including IR LEDs, resistance cartridge heaters, positive temperature coefficient heaters, or IR quartz heaters, as mentioned above. The heat may be deliberately generated and directed towards the area to be treated, as opposed to ambient heat in the clinical setting or byproduct heat from one or more operating mechanisms of the illuminator.

Administration of ALA

As indicated above, during photodynamic therapy, a total light dose is received by a patient over the course of treatment. The total light dose, in terms of J/cm$^2$, may be measured based on emitted irradiance (mW/cm$^2$) over time (in seconds). One example of a treatment method for precancerous lesions, such as actinic keratosis, by photodynamic therapy utilizing an adjustable illuminator described above in conjunction with ALA will now be described.

Essentially anhydrous ALA is admixed with a liquid diluent just prior to its use. The anhydrous ALA may be, for example, the hydrochloride salt of aminolevulinic acid (ALA), an endogenous 5-carbon aminoketone. The chemical name for ALA HCl, as employed in the embodiments disclosed herein, is 5-amino-4-oxopentanoic acid hydrochloride (molecular weight=167.59). ALA HCl is highly soluble in water. The structural formula of ALA HCl is represented below:

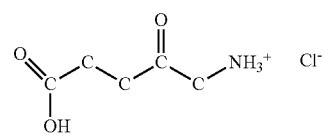

In at least one embodiment, the ALA is contained in powderized form inside a first ampule. In the first ampule, the amount of ALA as a dry solid may be between 300-400 mg. In at least one embodiment, the amount of ALA HCl is 354 mg. A second ampule contains a solution vehicle. The second ampule contains 1.5 mL of the solution vehicle. The solution vehicle comprises alcohol (i.e., alcohol as defined by the United States Pharmacopeia Convention) (ethanol content=48% v/v), water, laureth-4, isopropyl alcohol, and polyethylene glycol.

The first and second ampules are contained inside a plastic applicator. The first and second ampules may be crushed, e.g., by applying finger pressure, or inside a device configured to exert pressure on the ampule. Once the ampules are crushed, the ALA formerly contained in the first ampule contacts the solution formerly contained in the second ampule, and dissolves in the solution vehicle. The applicator in which the ampules were provided may be shaken so as to disperse and dissolve the powdered ALA in the solution vehicle. Once combined, the resulting solution is applied to the patient within 2 hours of preparation.

In some embodiments, the ALA may be provided in a composition such as a ready-to-use solution or a reconstituted powder for solution, gel, cream or lotion formulation. In another embodiment, the composition comprises 5-aminolevulinic acid hydrochloride in an amount of about 10% to about 70% w/w based on the total weight of the composition, preferably from about 20% to about 50% w/w based on the total weight of the composition, more preferably from about 30% to about 40% w/w based on the total weight of the composition.

In one embodiment, ALA may be applied in a topical composition with a concentration of 20%. The ALA admixture is topically applied to the lesions using a point applicator to control dispersion of the ALA admixture, in at least one embodiment, so as to achieve a substantially uniform wetting of the lesion surface with the ALA by contacting the ALA with the lesion surface. The term "substantial," or "substantially" as used herein, may refer to any value which lies within the range as defined by a variation of up to +15 from the average value. However, in other embodiments, the ALA may be applied digitally (i.e., by first disposing the ALA on the gloved fingertips of a practitioner, who then dabs the ALA on the region to be treated), or with a tool such as a spatula.

Occlusion with Barrier

Following application of the ALA to the region to be treated (i.e., the lesion), the region to be treated may be occluded with a polymer barrier. For example, as shown in FIG. 3, a polymer barrier 200 is wrapped around a region to be treated 300. While the exemplary embodiment shown in FIG. 3 depicts the barrier 200 as encircling the region 300, it should be understood that in certain embodiments, the barrier 200 may only occlude a portion of the region 300. Further, while barrier 200 is depicted as substantially cylindrical (e.g., so as to form a sleeve around region 300), the barrier 200 may have a variety of shapes.

Figure 4:
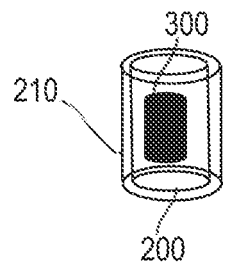
FIG. 4 shows a representative region to be treated in accordance with an exemplary embodiment.

The barrier 200 is shown with a clearance from the region 300 purely for ease of illustration in FIGS. 3 and 4. In at least one embodiment, however, the barrier 200 clings or adheres to the region 300 such that there is effectively no clearance between the barrier 200 and the region 300. The polyethylene barrier may have electrostatic properties that provide an adhesive clinging effect such that the barrier tends to stay close to the surface of the skin, even for prolonged periods. Such an effect may be particularly enhanced when the skin is wetted with the topical solution, i.e., when the treatment site is first wetted with the topical solution, and the barrier 200 is then applied directly on the wetted treatment site.

Experimental results confirmed that employing low density polyethylene (LDPE) for barrier 200 resulted in lower water loss rates and a superior degree of occlusion. In particular, embodiments with low density polyethylene barriers 200 were particularly effective for photodynamic therapy.

Figure 5:
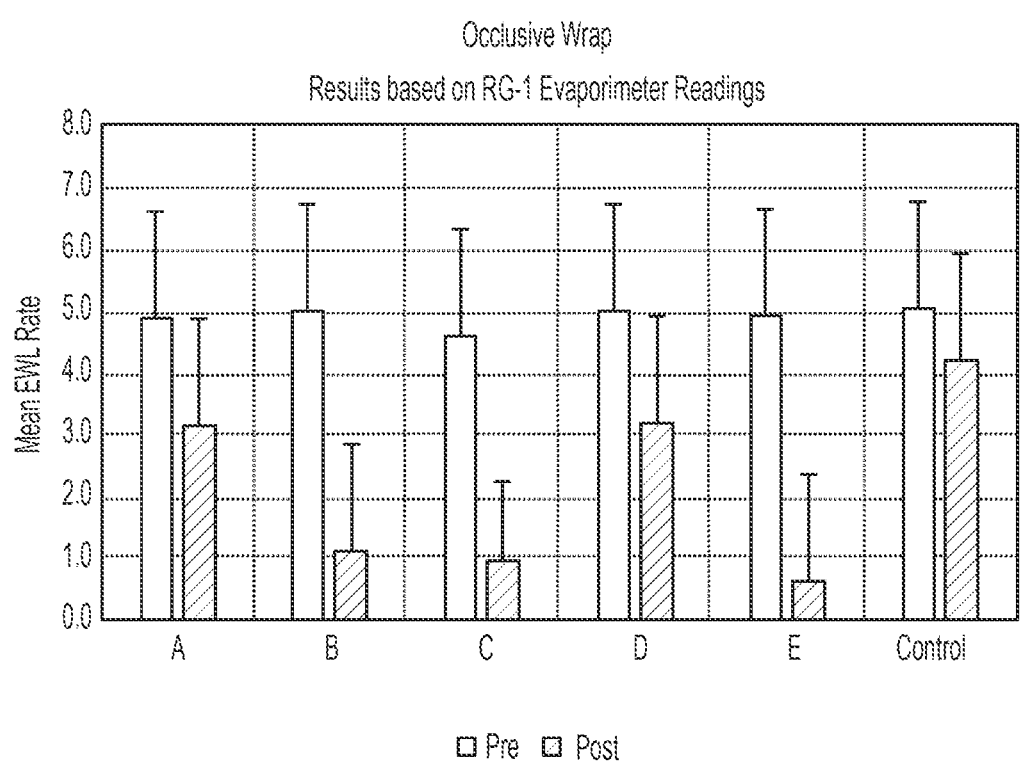
FIG. 5 depicts evaporative water loss rates for a plurality of materials, in accordance with at least one embodiment.

FIG. 5 depicts evaporative water loss rates for a plurality of materials A-E as summarized below in Table 1. The LDPE barriers were found to be especially conducive to retaining water and allowing for greater penetration of the ALA into the region to be treated.

TABLE 1

Barrier Materials A-E

| Material Code | Name | Distributor or Manufacturer | Material Description |
|---|---|---|---|
| A | Tegaderm ™, Style 1629 | 3M | Polyurethane |
| B | Glad ® Press'n Seal ® | The Glad Products Company | LDPE |
| C | Glad ® Cling Wrap | The Glad Products Company | LDPE |
| D | Stretch-Tite ® | Polyvinyl Films, Inc. | Polyvinylidene chloride (PVdC) |
| E | Saran ™ Premium Wrap | SC Johnson | LDPE |

The measured water loss rates shown in FIG. 5 (and FIG. 7, discussed below) are transepidermal water loss rates measured on the dorsal forearms, measured both before and after the barrier 200 had been worn for 3 hours. The baseline water loss was measured for approximately 30 subjects, after a minimum 25-minute acclimation period in a controlled environment with less than 50% relative humidity and a temperature between 19-22 deg. Celsius. Such measurements correspond to the bar plots labeled "pre" in FIGS. 5 and 7. The subjects had mild to moderate photodamage on their dorsal forearms. The measurements were made using a calibrated RG1 Evaporimeter System (made by cyberDERM, Inc. of Broomall, PA) with DermaLab® transepidermal water loss probes (made by Cortex Technology of Hadsund, Denmark).

A vapor pressure gradient estimation method was used. The probes measure the temperature and relative humidity at fixed points along the skin, allowing derivation of a value corresponding to evaporative water loss in $gm/m^2hr$. Sampling was performed at 4 inputs/second. The baseline measurements indicate the barrier properties of the stratum corneum of each subject, prior to applying barrier 200 to the stratum corneum. The measurements taken 3 hours after application of the barrier 200 are indicative of the barrier properties of the materials shown in Tables 1-2. Such measurements correspond to the bar plots labeled "post" in FIGS. 5 and 7. Each barrier 200 was cut so as to cover a test site area of 5 cm by 5 cm prior to application. The barrier 200 was secured with hypoallergenic medical tape for the purpose of testing. An area of the subjects' skin without the barrier 200 was measured as a control.

Figure 6:
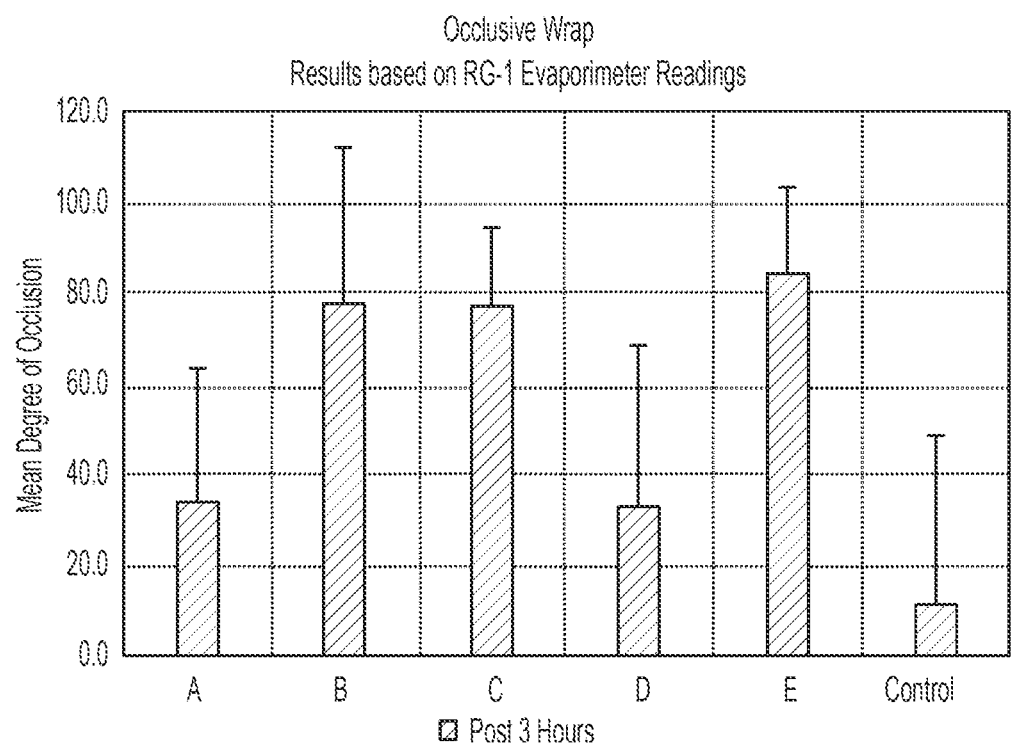
FIG. 6 depicts the degree of occlusion for a plurality of materials, in accordance with at least one embodiment.

FIG. 6 depicts degrees of occlusion for a plurality of materials in accordance with at least one embodiment. More specifically, FIG. 6 depicts the degree of occlusion for the materials shown in FIG. 5 and summarized above in Table 1. The degree of occlusion corresponds to the decrease in evaporative water loss rate when the subject wore the barrier 200 as compared to the baseline evaporative water loss rate. As indicated in FIG. 6, barrier material E, for example, blocked approximately 85% or more of the water vapor from evaporating from the skin surface. In one embodiment, a polymeric barrier having a degree of occlusion more than 65% is particularly effective for photodynamic therapy. In one embodiment, a polymeric barrier having a degree of occlusion more than 75% is particularly effective for photodynamic therapy. Greater occlusivity of LDPE materials such as material E enhances the penetration of ALA into the tissue by minimizing transepidermal water loss from the treatment area. The tissue may be skin, in particular, the stratum corneum, or other tissue of a human subject.

Similar to material E, materials B and C blocked approximately 75% of the water vapor from evaporating from the skin surface. Materials A and D, on the other hand, appeared to be semi-occlusive barriers.

Figure 7:
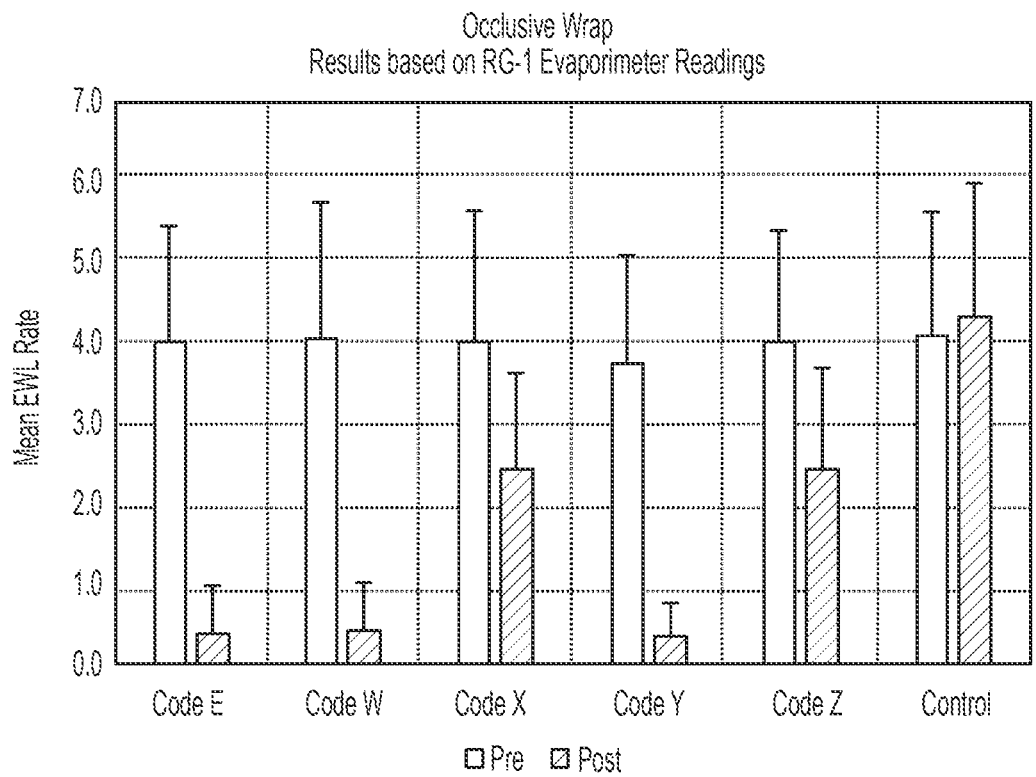
FIG. 7 depicts evaporative water loss rates for a plurality of materials, in accordance with at least one embodiment.

FIG. 7 depicts evaporative water loss rates for a plurality of materials in accordance with at least one embodiment. More specifically, FIG. 7 depicts evaporative water loss rates for a plurality of materials W-Z and E as summarized below in Table 2. Barrier material E was the same material as shown in Table 1 and discussed above. Materials W-Z included LDPE and polyvinylidene chloride.

TABLE 2

Barrier Materials W-Z and E

| Material Code | Name | Distributor or Manufacturer | Material Description |
|---|---|---|---|
| W | Best-Yet Clear Plastic Wrap | C&S Wholesale Grocers, Inc. | LDPE |
| X | Boardwalk ® PVC Food Wrap Film, BWK7204 | Boardwalk | PVdC |
| Y | Shurfine ® Strong and Stretchy ® Plastic Wrap | Western Family Foods, Inc. | LDPE |
| Z | Premium Plastic Wrap | Foodhold USA, LLC | PVdC |
| E | Saran ™ Premium Wrap | SC Johnson | LDPE |

Figure 8:
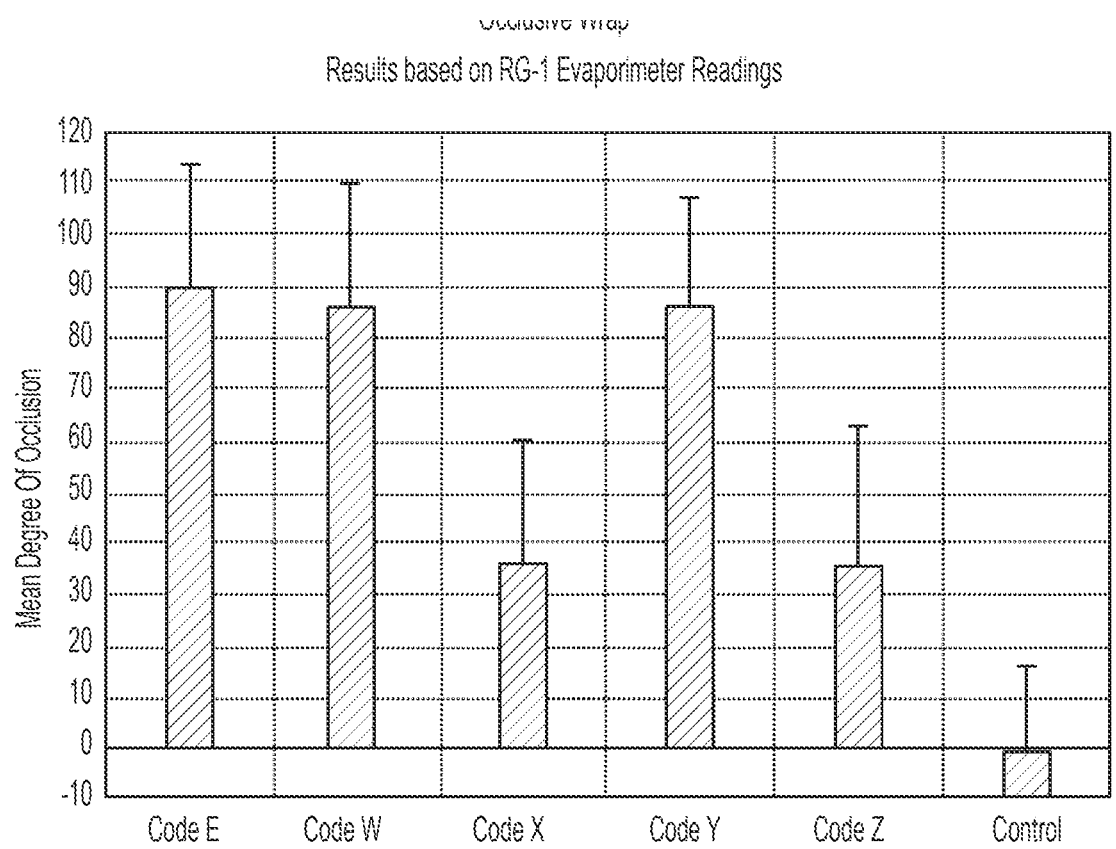
FIG. 8 depicts the degree of occlusion for a plurality of materials, in accordance with at least one embodiment.

FIG. 8 depicts degrees of occlusion for a plurality of materials in accordance with at least one embodiment. More specifically, FIG. 8 depicts the degree of occlusion for the materials shown in FIG. 7 and summarized above in Table 2. As seen in FIG. 8, materials E, W, and Y were significantly more occlusive than materials X and Z. Materials X and Z block only approximately 35% of water vapor from evaporating and are thus semi-occlusive in nature. Material E, due to its flexible nature, easily wraps around the treatment site, which may promote water retention.

FIG. 9 is a table containing baseline water loss data for the materials referred to in FIGS. 5-6. In particular, FIG. 9 provides the baseline measurements for each subject for each material A-E shown in Table 1, including mean and standard deviation values. FIG. 10 is a table containing water loss data following three hours of wear time for the materials referred to in FIGS. 5-6. FIG. 11 is a table containing occlusion data for the materials referred to in FIGS. 5-6. FIG. 12 is a table containing baseline water loss data for the materials referred to in FIGS. 7-8. FIG. 13 is a table containing water loss data following three hours of wear time for the materials referred to in FIGS. 7-8. FIG. 14 is a table containing occlusion data for the materials referred to in FIGS. 7-8.

As discussed above, the barrier 200 is used to occlude at least a portion of the region to be treated, e.g., all or part of the dorsal surface of the hand. In some embodiments, and particularly for larger treatment areas, such as the forearm, an additional structure may be provided to secure the barrier 200 in place. The low density polyethylene wrap may be secured in place with a dressing 210, shown in FIG. 4. In one embodiment, the dressing 210 is a surgical netting such as Surgilast® Tubular Elastic Dressing Retainer made by Derma Sciences Inc. of Plainsboro, New Jersey. The dressing 210 may be a tubular elastic stretch net designed to serve as a secondary dressing, which applies a relatively light pressure to keep barrier 200 securely in place without adhesive tape. That is, the secondary dressing 210 may exert slight compressive pressure on the barrier 200. The dressing 210 may be a sleeve which fits over and around barrier 200. In some embodiments, the secondary dressing and/or tape may be applied. Following application of the ALA and occlusion, treatment may be carried out in accordance with the exemplary implementations described below.

Treatment Protocols

Once the ALA is applied to the upper extremities, the upper extremities may be occluded for no more than three hours prior to light treatment. For example, the extremities may be occluded for 2-3 hours. As indicated above, the ALA is a porphyrin precursor which, when used as part of photodynamic therapy, may treat various conditions including minimally to moderately thick actinic keratoses of the face, scalp or the upper extremities. Accordingly, in at least one embodiment, one or more of a portion of the face, a portion or all of the scalp, or a portion or all of one or more of the upper extremities may be covered in an occlusive barrier.

Where the ALA is used to treat lesions of the face and scalp without the application of an occlusive barrier, following application of the ALA, formation of photosensitive porphyrin and photosensitization of the treated lesions occurs after 14-18 hours. Between 14 and 18 hours after administration of the ALA, the lesions are irradiated by an illuminator. The illuminator may, for example, irradiate the lesions with a uniform intensity blue light for a prescribed period. According to a preferred treatment, the visible light has a nominal wavelength of 417±5 nm.

The time period for illumination where the ALA is used to treat a lesion on an upper extremity can be significantly shorter when performed with the application of an occlusive barrier than for the face or scalp sites. The time period is approximately 3 hours between (1) application of ALA to the upper extremities and occlusion, and (2) the illumination of the upper extremities. If the occlusion time exceeds three hours for some treatment areas, then the skin where the ALA is applied may experience irritation. Excessive irritation may be marked by the presence of itching spots, wheals, flares, or other indicia, including symptoms persisting after the treatment session has ended. In particular, excessive irritation is marked by adverse cutaneous events such as scaling, crusting, ulceration, rashes, scabbing, tenderness and itching, for example. Three hours represents the nominal maximum time under which the upper extremity should be occluded following application of ALA, so as to avoid such excessive irritation while maintaining therapeutic efficacy. Therapeutic efficacy is the clearance of actinic keratosis lesion 12 weeks after PDT. The time period between the application of ALA to other body parts (other than the face, scalp and upper extremities) and illumination may be 3 hours, in some embodiments.

Once the occlusive barrier 200 is removed, light treatment as described above may be performed, e.g., application of red and/or blue light for a light dose of 10 J/cm$^2$. For example, once the barrier 200 is removed within 3 hours of being applied, blue light may be applied to the exposed treatment area to deliver a light dose of 10 J/cm$^2$, or red light may be applied for a 10 J/cm$^2$ to 75 J/cm$^2$ light dose. In some embodiments, the light may be delivered while the treatment site is still occluded. In some embodiments, light and heat may be delivered while the treatment site is still occluded.

To treat facial lesions, an illuminator as described above may be positioned such that the region to be treated is between 2 to 4 inches from a surface of the illuminator, with the patient's nose not less than 2 inches from the illuminator surface, and the forehead and cheeks no more than 4 inches from the surface. The sides of the patient's face and the patient's ears should be no closer than 2 inches from the illuminator surface.

To treat scalp lesions, an illuminator as described above may be positioned such that the region to be treated is between 2 to 4 inches from a surface of the illuminator, with the patient's scalp not less than 2 inches from the illuminator surface, and no more than 4 inches from the surface. The sides of the patient's face and the patient's ears should be no closer than 2 inches from the illuminator surface.

To treat lesions on the upper extremities, such as the dorsal surface of the hand or the forearms, an illuminator as described above may be positioned such that the region to be treated is between 2 to 4 inches from a surface of the illuminator. Equipment (e.g., a table) may be used to support the upper extremity during light treatment so as to enhance the patient's comfort and stabilize the region to be treated.

Two open-label, pharmacokinetic studies were carried out to evaluate the potential for systemic exposure of ALA and ALA and protoporphyrin IX (PpIX) when applied topically under occlusion, in a maximal use setting in patients with multiple actinic keratoses (AK) lesions on the upper extremities. In accordance with at least one embodiment, a 20% w/w topical composition of 5-aminolevulinic acid (ALA) was directly applied topically via an applicator to the upper extremities of the patients followed by covering with an occlusive, polyethylene film for a 3 hour incubation period. Light treatment was administered after the incubation period. Each subject received 10 J/cm$^2$ of visible blue light delivered at 10 mW/cm$^2$.

In the first of the two studies, a total of 29 participants were enrolled. The participants were males and non-pregnant females, aged 18 years or older. Each eligible subject had at least six Grade 1 or Grade 2 AK lesions on one upper extremity treatment area and at least 12 Grade 1 or Grade 2 AK lesions on the other upper extremity treatment area. The subjects received one treatment and were followed until week four after treatment. The treatment area, designated at baseline for the duration of the study, was the extensor surface of both distal upper extremities, as defined in the protocol (i.e., the dorsal hands/forearms). In the second of the two studies, a total of 14 participants were enrolled. Males and non-pregnant females, aged 18 years or older, with at least six Grade 1 or Grade 2 AK lesions on one upper extremity treatment area and at least 12 Grade 1 or Grade 2 AK lesions on the other upper extremity treatment area, were eligible for the study.

The topical application of the ALA to the upper extremities resulted in lower systemic exposure to ALA and PpIX than intravenous and oral dosing. The method according to at least one embodiment includes application of up to two topical solution compositions each containing about 354 mg ALA. The dosing using the topical solution was compared to intravenous and oral dosing in an amount of about 100 mg ALA. As indicated above, strength of the ALA was about 20% by weight. The topical dosing was observed to result in a mean plasma concentration ($C_{max}$) value of ALA of less than about 110 ng/ml. The term "$C_{max}$" as used herein refers to maximum observed plasma concentrations based on actual values measured following study medication application.

In particular, following topical applications, the geometric mean maximum plasma concentration was about 98 ng/mL at a median of 2 hours following application, with the geometric mean area-under-the-curve ($AUC_t$) of 577 ng*h/mL, with variability from about 94% to about 170%. Following a baseline correction, the ALA geometric mean maximum plasma concentration was 80 ng/mL at a median of 2 hours, with a geometric mean $AUC_t$ of 282 ng*h/mL. In an embodiment, the topical solution, when applied in a strength of about 20% by weight, exhibits a geometric mean area under curve ($AUC_\tau$) value of ALA less than about 350 ng·hr/mL. The term "$AUC_t$," as used herein, refers to the area under the plasma concentration-time curve up to the last quantifiable/non-negative plasma concentration.

In another experiment, following topical applications, the geometric mean maximum plasma concentration was about 61 ng/ml at a median of 2 hours following application, with the geometric mean $AUC_t$ of 727 ng*h/mL, with variability from about 30% to about 152%. Following a baseline correction, the ALA geometric mean maximum plasma concentration was 39 ng/ml at a median of 2 hours, and a geometric mean $AUC_t$ of 182 ng*h/mL. The estimated bioavailability following topical application of 354 mg ALA with occlusion was about 1.0%. In one embodiment, the systemic bioavailability following topical application of 354 mg ALA HCl is less than about 5%. The term "bioavailability" as used herein refers to the rate and extent of absorption and is determined by $AUC_\tau$ and $C_{max}$ values.

In accordance with at least one embodiment, a method of photodynamic therapy was carried out to treat lesions on the upper extremities in a multi-center randomized, parallel-group, evaluator-blinded and vehicle-controlled study of 269 patients with 4-15 mild to moderate actinic keratoses. The actinic keratoses were present on the upper extremities, more specifically, on the dorsal surface of the hands and/or the forearm area between the elbow and the base of the fingers. Subjects ranged from 45 to 90 years of age (mean 68 years) and 90% had Fitzpatrick Skin Type I, II or III. Subjects were randomized to treatment in a 1:1 ratio. ALA was applied to lesions on the dorsal surface of one hand or the forearm for each subject, and the dorsal surface of the hand or the forearm was then occluded with low density polyethylene barrier for three hours. Following removal of the low density polyethylene barrier, a 10 J/cm$^2$ dose of blue light was delivered at 10 mW/cm$^2$, with treatment repeated after 8 weeks if any lesion(s) remained in the treatment area.

Complete clearance (i.e., resolution of the actinic keratoses) was achieved by 31% of the subjects (that is, 42 out of 135 subjects) receiving ALA. Complete clearance was achieved at twelve weeks after initial treatment, as compared to 13% of subjects (that is, 17 out of 134 subjects) receiving only the solution vehicle (without the ALA). Of the subjects who achieved complete clearance at twelve weeks, a twelve-month follow-up evaluation was performed, which indicated that those subjects had a recurrence rate of 58%. The recurrence rate corresponds to the percentage of subjects with at least one recurrent lesion during the 12 month follow up period following the evaluation at twelve weeks who had previously achieved complete clearance at twelve weeks following treatment.

The present disclosure thus provides a method for photodynamically treating a surface of a patient, and occluding the patient's skin as part of treatment. The patient may be illuminated to treat actinic keratosis, acne, photo-damaged skin, cancer, warts, psoriasis, or other dermatological conditions.

While this specification contains certain specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

It is important to note that the construction and arrangement of the illuminator system shown in the various example implementations are illustrative only and not restrictive in character. All changes and modifications that come within the spirit and/or scope of the described implementations are desired to be protected. It should be understood that some features may not be necessary and implementations lacking the various features may be contemplated as within the scope of the disclosure, the scope being defined by the claims that follow. When the language "a portion" is used the item can include a portion and/or the entire item unless specifically stated to the contrary.

Additional advantages and modifications will readily occur to those skilled in the art. Therefore, the invention in its broader aspects is not limited to the specific details and representative devices and methods, shown and described herein. Accordingly, various modifications may be made without departing from the spirit and scope of the general inventive concept as defined by the appended claims and their equivalents.

What is claimed is:

1. A method of treating a lesion, the method comprising:
providing, via an applicator, a topical composition comprising 5-aminolevulinic acid (ALA);
applying the topical composition comprising the ALA onto a portion of skin containing the lesion, the portion of skin being on an extensor surface of a patient's body, wherein applying the topical composition via the applicator comprises controlling a dispersion of the topical composition;
providing, via the dispersion of the topical composition, uniform wetting of the portion of skin containing the lesion;
incubating the portion of the skin containing the lesion;
applying a barrier directly on the wetted portion of the skin; and
irradiating, via a light source, the portion of skin for a first time period.

2. The method of claim 1, further comprising determining an accumulation of protoporphyrin IX (PpIX) in the treatment area.

3. The method of claim 1, wherein the barrier comprises a polyethylene barrier or a foil barrier.

4. The method of claim 1, wherein a concentration of the ALA within the topical composition is 20% w/w or 10% w/w.

5. The method of claim 1, wherein irradiating the portion of skin comprises irradiating the portion of skin with a first light wavelength and subsequently irradiating the portion of skin with a second light wavelength.

6. The method of claim 5, wherein the first light wavelength corresponds to blue light and the second light wavelength corresponds to red light.

* * * * *